(12) United States Patent
Fangrow

(10) Patent No.: US 9,186,494 B2
(45) Date of Patent: *Nov. 17, 2015

(54) MEDICAL CONNECTOR

(71) Applicant: ICU Medical, Inc., San Clemente, CA (US)

(72) Inventor: Thomas F. Fangrow, Mission Viejo, CA (US)

(73) Assignee: ICU Medical, Inc., San Clemente, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/268,489

(22) Filed: May 2, 2014

(65) Prior Publication Data

US 2015/0011979 A1    Jan. 8, 2015

Related U.S. Application Data

(63) Continuation of application No. 13/205,463, filed on Aug. 8, 2011, now abandoned, which is a continuation of application No. 12/917,412, filed on Nov. 1, 2010, now abandoned, which is a continuation of application (Continued)

(51) Int. Cl.
*A61M 25/16* (2006.01)
*A61M 39/26* (2006.01)
(Continued)

(52) U.S. Cl.
CPC .............. *A61M 39/26* (2013.01); *A61M 39/10* (2013.01); *A61M 39/045* (2013.01); *A61M 2039/263* (2013.01); *A61M 2039/266* (2013.01); *Y10T 29/49826* (2013.01)

(58) Field of Classification Search
CPC ............................ A61M 39/045; A61M 39/26

USPC .................................. 604/533–284, 246–256
See application file for complete search history.

(56) References Cited

U.S. PATENT DOCUMENTS 274,447 A    3/1883    Kennish
1,578,517 A    3/1926    Hein
(Continued)

FOREIGN PATENT DOCUMENTS

CA    1 105 959    7/1981
CA    2 149 725    11/1995
(Continued)

OTHER PUBLICATIONS

U.S. Appl. No. 08/767,587, filed Dec. 16, 1996, Lopez et al.

(Continued)

*Primary Examiner* — Phillip Gray
(74) *Attorney, Agent, or Firm* — Knobbe, Martens, Olson & Bear, LLP

(57) ABSTRACT

A soft grip medical connector comprises a housing with an upstream end, a downstream end and a lumen extending through a central portion thereof. A flexible member comprises a valve portion integrally formed with a sleeve portion. The valve portion is positioned within a section of the housing and is configured to control a flow of fluid through the housing lumen. The sleeve is inverted to envelope at least a portion of the outer surface of the housing. In some embodiments the gripping portion is integrally formed with the valve portion. In some embodiments, the connector is also generally configured to create a positive pressure in a catheter lumen upon removal of a syringe or other medical device from the upstream end of the connector. Methods of making a medical fluid connector generally comprise forming a valve member with a sleeve extending there from, and assembling the valve, sleeve and housing.

30 Claims, 19 Drawing Sheets

Related U.S. Application Data

No. 11/417,675, filed on May 3, 2006, now Pat. No. 7,824,393, which is a continuation of application No. 11/267,822, filed on Nov. 4, 2005, now abandoned.

(60) Provisional application No. 60/625,644, filed on Nov. 5, 2004, provisional application No. 60/654,250, filed on Feb. 18, 2005.

(51) Int. Cl.
*A61M 39/10* (2006.01)
*A61M 39/04* (2006.01)

(56) References Cited

U.S. PATENT DOCUMENTS

| | | |
|---|---|---|
| 1,923,501 A | 8/1933 | Perry |
| 2,210,098 A | 8/1940 | Ravenscroft |
| 2,289,677 A | 7/1942 | Perelson |
| 2,577,780 A | 12/1951 | Lockhart |
| 2,756,282 A | 7/1956 | Deane |
| 2,756,740 A | 7/1956 | Deane |
| 2,809,665 A | 10/1957 | Crowe |
| 2,847,995 A | 8/1958 | Adams |
| 2,999,499 A | 9/1961 | Willet |
| 3,134,380 A | 5/1964 | Armao |
| 3,135,261 A | 6/1964 | Carroll |
| 3,171,412 A | 3/1965 | Braun |
| 3,176,021 A | 3/1965 | Volungis et al. |
| 3,191,655 A | 6/1965 | McCord |
| 3,193,154 A | 7/1965 | Bross et al. |
| 3,334,860 A | 8/1967 | Bolton, Jr. |
| 3,352,531 A | 11/1967 | Kilmarx |
| 3,354,881 A | 11/1967 | Bloch |
| 3,385,301 A | 5/1968 | Harautuneian |
| 3,502,097 A | 3/1970 | Muller |
| 3,534,771 A | 10/1970 | Eyerdam et al. |
| 3,570,484 A | 3/1971 | Steer et al. |
| 3,630,199 A | 12/1971 | Gangarosa |
| 3,648,684 A | 3/1972 | Barnwell et al. |
| 3,659,602 A | 5/1972 | Cloyd |
| 3,717,174 A | 2/1973 | Dewall |
| 3,726,282 A | 4/1973 | Patel |
| 3,788,519 A | 1/1974 | Mengel |
| 3,830,241 A | 8/1974 | Dye et al. |
| 3,831,629 A | 8/1974 | Mackal et al. |
| 3,852,385 A | 12/1974 | Huggins |
| 3,861,388 A | 1/1975 | Vaughn |
| 3,889,675 A | 6/1975 | Stewart |
| 3,896,853 A | 7/1975 | Bernhard |
| 3,965,910 A | 6/1976 | Fisher |
| 3,974,832 A | 8/1976 | Kruck |
| 3,976,063 A | 8/1976 | Henneman et al. |
| 3,976,073 A | 8/1976 | Quick et al. |
| 3,977,403 A | 8/1976 | Patel |
| 3,986,508 A | 10/1976 | Barrington |
| 3,993,063 A | 11/1976 | Larrabee |
| 3,994,293 A | 11/1976 | Ferro |
| 4,005,710 A | 2/1977 | Zeddies et al. |
| 4,019,512 A | 4/1977 | Tenczar |
| 4,022,205 A | 5/1977 | Tenczar |
| 4,040,420 A | 8/1977 | Speer |
| 4,076,285 A | 2/1978 | Martinez |
| 4,079,738 A | 3/1978 | Dunn et al. |
| 4,080,965 A | 3/1978 | Phillips |
| 4,121,585 A | 10/1978 | Becker, Jr. |
| 4,128,098 A | 12/1978 | Bloom et al. |
| 4,133,441 A | 1/1979 | Mittleman et al. |
| 4,143,853 A | 3/1979 | Abramson |
| 4,149,535 A | 4/1979 | Volder |
| 4,161,949 A | 7/1979 | Thanawalla |
| 4,186,775 A | 2/1980 | Muroi |
| 4,187,846 A | 2/1980 | Lolachi et al. |
| 4,191,183 A | 3/1980 | Mendelson |
| 4,198,983 A | 4/1980 | Becker et al. |
| 4,200,096 A | 4/1980 | Charvin |
| 4,214,779 A | 7/1980 | Losell |
| 4,219,912 A | 9/1980 | Adams |
| 4,243,034 A | 1/1981 | Brandt |
| 4,257,416 A | 3/1981 | Prager |
| D259,278 S | 5/1981 | McCaw et al. |
| 4,294,249 A | 10/1981 | Sheehan et al. |
| 4,294,250 A | 10/1981 | Dennehey |
| 4,296,949 A | 10/1981 | Muetterties et al. |
| 4,306,705 A | 12/1981 | Svensson |
| 4,324,239 A | 4/1982 | Gordon et al. |
| 4,328,802 A | 5/1982 | Curley et al. |
| 4,329,987 A | 5/1982 | Rogers et al. |
| 4,334,551 A | 6/1982 | Pfister |
| 4,338,933 A | 7/1982 | Bayard et al. |
| 4,342,315 A | 8/1982 | Jackson |
| 4,346,703 A | 8/1982 | Dennehey et al. |
| 4,362,156 A | 12/1982 | Feller et al. |
| 4,387,879 A | 6/1983 | Tauschinski |
| RE31,315 E | 7/1983 | Jenkins et al. |
| 4,392,851 A | 7/1983 | Elias |
| 4,405,163 A | 9/1983 | Voges et al. |
| 4,405,312 A | 9/1983 | Gross et al. |
| 4,411,662 A | 10/1983 | Pearson |
| 4,417,890 A | 11/1983 | Dennehey et al. |
| 4,421,296 A | 12/1983 | Stephens |
| 4,429,856 A | 2/1984 | Jackson |
| 4,432,759 A | 2/1984 | Gross et al. |
| 4,432,765 A | 2/1984 | Oscarsson |
| 4,439,188 A | 3/1984 | Dennehey et al. |
| 4,439,193 A | 3/1984 | Larkin |
| 4,449,693 A | 5/1984 | Gereg |
| 4,457,749 A | 7/1984 | Bellotti et al. |
| 4,483,368 A | 11/1984 | Panthafer |
| 4,508,367 A | 4/1985 | Oreopoulos et al. |
| 4,511,359 A | 4/1985 | Vaillancourt |
| 4,512,766 A | 4/1985 | Vailancourt |
| 4,564,054 A | 1/1986 | Gustavsson |
| 4,592,356 A | 6/1986 | Gutierrez |
| 4,607,868 A | 8/1986 | Harvey et al. |
| 4,610,469 A | 9/1986 | Wolff-Mooij |
| 4,617,012 A | 10/1986 | Vaillancourt |
| 4,619,640 A | 10/1986 | Potolsky et al. |
| 4,623,068 A | 11/1986 | Brown et al. |
| 4,645,494 A | 2/1987 | Lee et al. |
| 4,666,429 A | 5/1987 | Stone |
| 4,673,400 A | 6/1987 | Martin |
| 4,676,228 A | 6/1987 | Krasner et al. |
| 4,683,916 A | 8/1987 | Raines |
| 4,706,487 A | 11/1987 | Bandou et al. |
| 4,710,168 A | 12/1987 | Schwab et al. |
| 4,725,267 A | 2/1988 | Vaillancourt |
| 4,730,635 A | 3/1988 | Linden |
| 4,752,292 A | 6/1988 | Lopez et al. |
| D296,592 S | 7/1988 | Wellenstam |
| 4,758,224 A | 7/1988 | Siposs |
| 4,759,756 A | 7/1988 | Forman et al. |
| 4,775,369 A | 10/1988 | Schwartz |
| 4,778,447 A | 10/1988 | Velde et al. |
| 4,778,453 A | 10/1988 | Lopez |
| 4,781,702 A | 11/1988 | Herrli |
| 4,804,015 A | 2/1989 | Albinsson |
| D300,177 S | 3/1989 | Bellotti et al. |
| 4,810,241 A | 3/1989 | Rogers |
| 4,813,938 A | 3/1989 | Raulerson |
| 4,819,684 A | 4/1989 | Zaugg et al. |
| 4,832,214 A | 5/1989 | Schrader et al. |
| 4,834,664 A | 5/1989 | Lin |
| 4,834,716 A | 5/1989 | Ogle, II |
| D303,013 S | 8/1989 | Konopka |
| 4,874,377 A | 10/1989 | Newgard et al. |
| 4,878,897 A | 11/1989 | Katzin |
| 4,880,414 A | 11/1989 | Whipple |
| 4,889,527 A | 12/1989 | Herrli |
| 4,915,687 A | 4/1990 | Sivert |
| 4,917,668 A | 4/1990 | Haindl |
| 4,919,167 A | 4/1990 | Manska |
| 4,928,212 A | 5/1990 | Benavides |
| 4,934,657 A | 6/1990 | Dodson |

(56) References Cited

U.S. PATENT DOCUMENTS

| | | | |
|---|---|---|---|
| 4,943,896 A | 7/1990 | Johnson | |
| 4,946,445 A | 8/1990 | Lynn | |
| 4,963,133 A | 10/1990 | Whipple | |
| 4,964,855 A | 10/1990 | Todd et al. | |
| 4,966,199 A | 10/1990 | Ruschke | |
| 4,969,883 A | 11/1990 | Gilbert et al. | |
| D314,050 S | 1/1991 | Sone | |
| 4,985,399 A | 1/1991 | Matsuda et al. | |
| 4,987,181 A | 1/1991 | Bichon et al. | |
| 4,991,413 A | 2/1991 | Arnaldo | |
| 4,991,629 A | 2/1991 | Ernesto et al. | |
| 4,998,713 A | 3/1991 | Vaillancourt | |
| 4,998,927 A | 3/1991 | Vaillancourt | |
| 5,006,114 A | 4/1991 | Rogers et al. | |
| 5,009,490 A | 4/1991 | Kouno et al. | |
| 5,018,532 A | 5/1991 | Etheredge, III | |
| 5,024,657 A | 6/1991 | Needham et al. | |
| 5,031,675 A | 7/1991 | Lindqren | |
| 5,041,087 A | 8/1991 | Loo et al. | |
| 5,046,456 A | 9/1991 | Heyman et al. | |
| 5,049,128 A | 9/1991 | Duquette | |
| D321,250 S | 10/1991 | Jepson et al. | |
| D321,251 S | 10/1991 | Jepson et al. | |
| 5,061,253 A | 10/1991 | Yoshida | |
| 5,064,416 A | 11/1991 | Newgard | |
| 5,065,783 A | 11/1991 | Ogle, II | |
| 5,071,411 A | 12/1991 | Hillstead | |
| 5,098,385 A | 3/1992 | Walsh | |
| 5,098,405 A | 3/1992 | Peterson et al. | |
| 5,098,406 A | 3/1992 | Sawyer | |
| 5,100,394 A | 3/1992 | Dudar et al. | |
| 5,108,380 A | 4/1992 | Heritze et al. | |
| 5,114,408 A | 5/1992 | Fleischhaker et al. | |
| 5,116,361 A | 5/1992 | Kim et al. | |
| 5,122,123 A | 6/1992 | Vaillancourt | |
| 5,125,915 A | 6/1992 | Berry et al. | |
| 5,135,489 A | 8/1992 | Jepson et al. | |
| 5,137,524 A | 8/1992 | Lynn et al. | |
| 5,147,333 A | 9/1992 | Raines | |
| 5,154,703 A | 10/1992 | Bonaldo | |
| 5,158,554 A | 10/1992 | Jepson et al. | |
| 5,163,922 A | 11/1992 | McElveen, Jr. et al. | |
| 5,167,238 A | 12/1992 | Newman | |
| 5,167,636 A | 12/1992 | Clement | |
| 5,171,234 A | 12/1992 | Jepson et al. | |
| 5,180,761 A | 1/1993 | Shiao | |
| 5,188,620 A | 2/1993 | Jepson et al. | |
| 5,190,067 A | 3/1993 | Paradis et al. | |
| 5,199,947 A | 4/1993 | Lopez et al. | |
| 5,201,717 A | 4/1993 | Wyatt et al. | |
| 5,201,722 A | 4/1993 | Moorehead et al. | |
| 5,203,775 A | 4/1993 | Frank et al. | |
| 5,211,638 A | 5/1993 | Dudar et al. | |
| 5,215,538 A | 6/1993 | Larkin | |
| 5,221,271 A | 6/1993 | Nicholson et al. | |
| 5,224,515 A | 7/1993 | Foster et al. | |
| 5,242,393 A | 9/1993 | Brimhall et al. | |
| 5,242,423 A | 9/1993 | Goodsir et al. | |
| 5,242,425 A | 9/1993 | White et al. | |
| 5,242,432 A | 9/1993 | DeFrank | |
| 5,251,873 A | 10/1993 | Atkinson et al. | |
| 5,253,842 A | 10/1993 | Huebscher et al. | |
| 5,255,676 A | 10/1993 | Russo | |
| 5,256,155 A | 10/1993 | Yerlikaya et al. | |
| 5,267,966 A | 12/1993 | Paul | |
| 5,269,771 A | 12/1993 | Thomas et al. | |
| 5,273,533 A | 12/1993 | Bonaldo | |
| 5,280,876 A | 1/1994 | Atkins | |
| 5,284,475 A | 2/1994 | Mackal | |
| 5,290,254 A | 3/1994 | Vaillancourt | |
| 5,292,308 A | 3/1994 | Ryan | |
| 5,293,902 A | 3/1994 | Lapierie | |
| 5,295,657 A | 3/1994 | Atkinson | |
| 5,295,658 A | 3/1994 | Atkinson et al. | |
| 5,301,686 A | 4/1994 | Newman | |
| 5,306,265 A | 4/1994 | Ragazzi | |
| 5,312,083 A | 5/1994 | Ekman | |
| 5,312,377 A | 5/1994 | Dalton | |
| 5,322,518 A | 6/1994 | Schneider | |
| 5,324,270 A | 6/1994 | Kayan et al. | |
| 5,336,192 A | 8/1994 | Palestrant | |
| 5,342,316 A | 8/1994 | Wallace | |
| 5,342,326 A | 8/1994 | Peppel et al. | |
| 5,344,414 A | 9/1994 | Lopez et al. | |
| 5,348,542 A | 9/1994 | Ellis | |
| 5,353,837 A | 10/1994 | Faust | |
| 5,356,396 A | 10/1994 | Wyatt et al. | |
| 5,360,413 A | 11/1994 | Leason et al. | |
| 5,380,306 A | 1/1995 | Brinon | |
| 5,389,086 A | 2/1995 | Attermeier et al. | |
| 5,395,348 A | 3/1995 | Ryan | |
| 5,398,530 A | 3/1995 | Derman | |
| 5,401,245 A | 3/1995 | Haining | |
| 5,402,826 A | 4/1995 | Molnar et al. | |
| 5,402,982 A | 4/1995 | Atkinson et al. | |
| 5,407,437 A | 4/1995 | Heimreid | |
| 5,409,471 A | 4/1995 | Atkinson et al. | |
| 5,411,483 A | 5/1995 | Loomas et al. | |
| 5,411,499 A | 5/1995 | Dudar et al. | |
| 5,417,673 A | 5/1995 | Gordon | |
| 5,439,451 A | 8/1995 | Collinson et al. | |
| 5,439,452 A | 8/1995 | McCarty | |
| 5,441,487 A | 8/1995 | Vedder | |
| 5,442,941 A | 8/1995 | Kahonen et al. | |
| 5,456,676 A | 10/1995 | Nelson et al. | |
| 5,462,255 A | 10/1995 | Rosen et al. | |
| 5,470,319 A | 11/1995 | Mayer | |
| 5,474,544 A | 12/1995 | Lynn | |
| 5,480,393 A | 1/1996 | Bommarito | |
| 5,487,731 A | 1/1996 | Denton | |
| 5,501,426 A | 3/1996 | Atkinson et al. | |
| 5,501,526 A | 3/1996 | Asai et al. | |
| 5,509,433 A | 4/1996 | Paradis | |
| 5,514,116 A | 5/1996 | Vaillancourt et al. | |
| 5,520,665 A | 5/1996 | Fleetwood | |
| 5,522,804 A | 6/1996 | Lynn | |
| 5,533,708 A | 7/1996 | Atkinson et al. | |
| 5,533,996 A | 7/1996 | Murphey et al. | |
| 5,535,771 A | 7/1996 | Purdy et al. | |
| 5,535,785 A | 7/1996 | Werge et al. | |
| 5,540,661 A | 7/1996 | Tomisaka et al. | |
| 5,549,566 A | 8/1996 | Elias et al. | |
| 5,549,577 A | 8/1996 | Siegel et al. | |
| 5,549,651 A | 8/1996 | Lynn | |
| 5,555,908 A | 9/1996 | Edwards et al. | |
| 5,556,388 A | 9/1996 | Johlin, Jr. | |
| 5,562,632 A | 10/1996 | Davila et al. | |
| 5,569,235 A | 10/1996 | Ross et al. | |
| 5,573,516 A | 11/1996 | Tyner | |
| 5,577,706 A | 11/1996 | King | |
| 5,578,059 A | 11/1996 | Patzer | |
| 5,597,536 A | 1/1997 | Mayer | |
| 5,603,706 A | 2/1997 | Wyatt et al. | |
| 5,609,584 A | 3/1997 | Gettig et al. | |
| 5,616,129 A | 4/1997 | Mayer | |
| 5,616,130 A | 4/1997 | Mayer | |
| 5,617,897 A | 4/1997 | Myers | |
| 5,620,424 A | 4/1997 | Abramson | |
| 5,620,434 A | 4/1997 | Brony | |
| 5,624,414 A | 4/1997 | Boettger | |
| 5,632,735 A | 5/1997 | Wyatt et al. | |
| 5,639,810 A | 6/1997 | Smith, III et al. | |
| 5,660,205 A | 8/1997 | Epstein | |
| 5,669,891 A | 9/1997 | Vaillancourt | |
| 5,674,206 A * | 10/1997 | Allton et al. | 604/249 |
| 5,676,346 A | 10/1997 | Leinsing | |
| 5,685,866 A | 11/1997 | Lopez | |
| 5,690,612 A | 11/1997 | Lopez et al. | |
| 5,690,865 A | 11/1997 | Kindt-Larsen et al. | |
| 5,694,686 A | 12/1997 | Lopez | |
| 5,695,466 A | 12/1997 | Lopez et al. | |
| 5,699,821 A | 12/1997 | Paradis | |
| 5,700,248 A | 12/1997 | Lopez | |
| 5,728,751 A | 3/1998 | Patnaik | |

(56) References Cited

U.S. PATENT DOCUMENTS

| | | | |
|---|---|---|---|
| 5,730,418 A | 3/1998 | Feith et al. |
| 5,738,663 A | 4/1998 | Lopez |
| 5,749,861 A | 5/1998 | Guala et al. |
| 5,769,825 A | 6/1998 | Lynn |
| 5,775,671 A | 7/1998 | Cote, Sr. |
| 5,776,113 A | 7/1998 | Daugherty et al. |
| 5,782,816 A | 7/1998 | Werschmidt et al. |
| 5,788,215 A | 8/1998 | Ryan |
| 5,797,897 A | 8/1998 | Jepson et al. |
| 5,806,551 A | 9/1998 | Meloul et al. |
| 5,806,831 A | 9/1998 | Paradis |
| 5,807,348 A | 9/1998 | Zinger et al. |
| 5,817,069 A | 10/1998 | Arnett |
| 5,820,601 A | 10/1998 | Mayer |
| 5,833,213 A | 11/1998 | Ryan |
| 5,836,923 A | 11/1998 | Mayer |
| 5,839,715 A | 11/1998 | Leinsing |
| 5,843,046 A | 12/1998 | Motisi et al. |
| 5,846,233 A | 12/1998 | Lilley et al. |
| 5,865,807 A | 2/1999 | Blake, III |
| 5,873,862 A | 2/1999 | Lopez |
| 5,882,348 A | 3/1999 | Winterton et al. |
| 5,899,888 A | 5/1999 | Jepson et al. |
| 5,901,942 A | 5/1999 | Lopez |
| 5,911,710 A | 6/1999 | Barry et al. |
| 5,928,204 A | 7/1999 | Lopez |
| 5,935,620 A | 8/1999 | Baudin |
| 5,947,954 A | 9/1999 | Bonaldo |
| 5,954,313 A | 9/1999 | Ryan |
| 5,957,898 A * | 9/1999 | Jepson et al. | 604/256 |
| 5,967,490 A | 10/1999 | Pike |
| 5,979,868 A | 11/1999 | Wu et al. |
| 6,009,902 A | 1/2000 | Troiani et al. |
| 6,019,748 A * | 2/2000 | Lopez | 604/249 |
| 6,029,946 A | 2/2000 | Doyle |
| 6,036,171 A | 3/2000 | Weinheimer et al. |
| 6,039,302 A | 3/2000 | Cote, Sr. et al. |
| 6,048,335 A | 4/2000 | Mayer |
| 6,050,978 A | 4/2000 | Orr et al. |
| 6,063,062 A | 5/2000 | Paradis |
| 6,079,432 A | 6/2000 | Paradis |
| 6,089,541 A | 7/2000 | Weinheimer et al. |
| 6,113,068 A | 9/2000 | Ryan |
| 6,116,571 A | 9/2000 | Hettinger |
| 6,117,114 A | 9/2000 | Paradis |
| 6,132,403 A | 10/2000 | Lopez |
| 6,132,404 A | 10/2000 | Lopez |
| 6,142,446 A | 11/2000 | Leinsing |
| 6,152,900 A | 11/2000 | Mayer |
| 6,162,206 A | 12/2000 | Bindokas et al. |
| 6,162,251 A | 12/2000 | Kredovski |
| 6,168,137 B1 | 1/2001 | Paradis |
| 6,170,800 B1 | 1/2001 | Meloul et al. |
| 6,171,287 B1 | 1/2001 | Lynn |
| 6,177,037 B1 | 1/2001 | Mayer |
| 6,183,448 B1 | 2/2001 | Mayer |
| 6,189,859 B1 | 2/2001 | Rohrbough et al. |
| 6,206,861 B1 | 3/2001 | Mayer |
| 6,210,624 B1 | 4/2001 | Mayer |
| 6,213,996 B1 | 4/2001 | Jepson et al. |
| 6,228,065 B1 | 5/2001 | Lynn |
| 6,228,069 B1 | 5/2001 | Barth et al. |
| 6,245,048 B1 | 6/2001 | Fangrow et al. |
| 6,254,579 B1 | 7/2001 | Cogger et al. |
| 6,261,282 B1 | 7/2001 | Jepson et al. |
| 6,261,630 B1 | 7/2001 | Nazarova et al. |
| 6,279,783 B1 | 8/2001 | Brown et al. |
| 6,290,206 B1 | 9/2001 | Doyle |
| 6,299,131 B1 | 10/2001 | Ryan |
| 6,299,132 B1 | 10/2001 | Weinheimer |
| 6,325,782 B1 | 12/2001 | Lopez |
| 6,364,869 B1 | 4/2002 | Bonaldo |
| 6,428,520 B1 | 8/2002 | Lopez et al. |
| 6,444,324 B1 | 9/2002 | Yang et al. |
| 6,482,188 B1 | 11/2002 | Rogers et al. |
| D468,016 S | 12/2002 | Mosler et al. |
| 6,541,802 B2 | 4/2003 | Doyle |
| 6,543,745 B1 | 4/2003 | Enerson |
| 6,572,592 B1 | 6/2003 | Lopez |
| 6,585,229 B2 | 7/2003 | Cote, Sr. et al. |
| 6,595,964 B2 | 7/2003 | Finley et al. |
| 6,595,981 B2 | 7/2003 | Huet |
| 6,599,273 B1 | 7/2003 | Lopez |
| 6,605,076 B1 | 8/2003 | Jepson et al. |
| 6,609,696 B2 | 8/2003 | Enerson |
| 6,635,044 B2 | 10/2003 | Lopez |
| 6,651,956 B2 | 11/2003 | Miller |
| 6,656,517 B2 | 12/2003 | Michal et al. |
| 6,669,673 B2 | 12/2003 | Lopez |
| 6,669,681 B2 | 12/2003 | Jepson et al. |
| 6,673,053 B2 | 1/2004 | Wang et al. |
| 6,682,509 B2 | 1/2004 | Lopez |
| 6,689,109 B2 | 2/2004 | Lynn |
| 6,695,817 B1 * | 2/2004 | Fangrow, Jr. | 604/167.01 |
| 6,706,022 B1 | 3/2004 | Leinsing et al. |
| 6,712,791 B2 | 3/2004 | Lui et al. |
| 6,727,294 B2 | 4/2004 | Kanayama et al. |
| 6,740,063 B2 | 5/2004 | Lynn |
| 6,745,998 B2 | 6/2004 | Doyle |
| 6,755,391 B2 | 6/2004 | Newton et al. |
| 6,758,833 B2 | 7/2004 | Lopez |
| 6,783,709 B2 | 8/2004 | Harreld et al. |
| 6,802,490 B2 | 10/2004 | Leinsing |
| 6,808,161 B1 | 10/2004 | Hishikawa |
| 6,840,501 B2 | 1/2005 | Doyle |
| 6,848,139 B2 | 2/2005 | Simon et al. |
| 6,866,656 B2 | 3/2005 | Tingey et al. |
| 6,869,426 B2 | 3/2005 | Ganem |
| 6,871,838 B2 | 3/2005 | Raines et al. |
| 6,883,778 B1 | 4/2005 | Newton et al. |
| 6,892,998 B2 | 5/2005 | Newton |
| 6,908,459 B2 | 6/2005 | Harding et al. |
| 6,916,309 B2 | 7/2005 | Fangrow, Jr. |
| 6,932,795 B2 | 8/2005 | Lopez et al. |
| 6,964,406 B2 | 11/2005 | Doyle |
| 6,991,215 B2 | 1/2006 | Kiehne |
| 6,994,315 B2 | 2/2006 | Ryan et al. |
| 6,997,917 B2 | 2/2006 | Niedospial, Jr. et al. |
| 7,014,169 B2 | 3/2006 | Newton et al. |
| 7,025,744 B2 | 4/2006 | Utterberg et al. |
| 7,033,339 B1 | 4/2006 | Lynn |
| 7,037,302 B2 | 5/2006 | Vaillancourt |
| 7,044,441 B2 | 5/2006 | Doyle |
| 7,074,216 B2 | 7/2006 | Fowles et al. |
| 7,100,890 B2 | 9/2006 | Cote et al. |
| 7,104,520 B2 | 9/2006 | Leinsing et al. |
| 7,114,701 B2 | 10/2006 | Peppel |
| 7,125,396 B2 | 10/2006 | Leinsing et al. |
| 7,140,592 B2 | 11/2006 | Phillips |
| 7,184,825 B2 | 2/2007 | Leinsing et al. |
| 7,244,249 B2 | 7/2007 | Leinsing et al. |
| 7,252,652 B2 | 8/2007 | Moorehead et al. |
| 7,264,859 B2 | 9/2007 | Rouns et al. |
| 7,306,197 B2 | 12/2007 | Parrino et al. |
| 7,306,199 B2 | 12/2007 | Leinsing et al. |
| 7,314,061 B2 | 1/2008 | Peppel |
| 7,329,249 B2 | 2/2008 | Bonaldo |
| 7,335,182 B1 | 2/2008 | Hilaire |
| 7,357,792 B2 | 4/2008 | Newton et al. |
| 7,396,348 B2 | 7/2008 | Newton et al. |
| 7,422,369 B2 | 9/2008 | Bergman et al. |
| 7,470,261 B2 | 12/2008 | Lynn |
| 7,470,262 B2 | 12/2008 | Hiejima et al. |
| 7,497,848 B2 | 3/2009 | Leinsing et al. |
| 7,497,849 B2 | 3/2009 | Fangrow, Jr. |
| 7,510,545 B2 | 3/2009 | Peppel |
| 7,520,489 B2 | 4/2009 | Ruschke |
| 7,530,546 B2 | 5/2009 | Ryan |
| 7,563,243 B2 | 7/2009 | Mendels |
| 7,581,561 B2 | 9/2009 | Funamara et al. |
| 7,584,767 B2 | 9/2009 | Funamura et al. |
| 7,588,563 B2 | 9/2009 | Guala |
| 7,591,449 B2 | 9/2009 | Raines et al. |
| 7,601,141 B2 | 10/2009 | Dikeman et al. |

(56) References Cited

U.S. PATENT DOCUMENTS

| | | |
|---|---|---|
| 7,615,035 B2 | 11/2009 | Peppel |
| 7,628,774 B2 | 12/2009 | Fangrow, Jr. |
| 7,666,170 B2 | 2/2010 | Guala |
| 7,713,250 B2 | 5/2010 | Harding et al. |
| 7,717,886 B2 | 5/2010 | Lopez |
| 7,753,338 B2 | 7/2010 | Desecki |
| 7,753,892 B2 | 7/2010 | Newton et al. |
| 7,758,566 B2 | 7/2010 | Simpson et al. |
| 7,763,199 B2 | 7/2010 | Fangrow |
| 7,784,766 B2 | 8/2010 | Guala |
| 7,815,168 B2 | 10/2010 | Vangsness et al. |
| 7,837,658 B2 | 11/2010 | Cote, Sr. et al. |
| 7,857,284 B2 | 12/2010 | Kimball et al. |
| 7,857,285 B2 | 12/2010 | Lee et al. |
| 7,867,204 B2 | 1/2011 | Bartholomew et al. |
| 7,879,012 B2 | 2/2011 | Kane et al. |
| 7,914,502 B2 | 3/2011 | Newton et al. |
| 7,975,722 B2 | 7/2011 | Kiehne |
| 7,998,134 B2 | 8/2011 | Fangrow |
| D644,731 S | 9/2011 | Fangrow, Jr. |
| 8,105,314 B2 | 1/2012 | Fangrow |
| 8,177,760 B2 | 5/2012 | Rome et al. |
| 8,221,391 B2 | 7/2012 | Fangrow, Jr. |
| 8,286,657 B2 | 10/2012 | Belley et al. |
| 8,398,607 B2 | 3/2013 | Fangrow, Jr. |
| 8,403,894 B2 | 3/2013 | Lynn et al. |
| 8,409,165 B2 | 4/2013 | Niedospial, Jr. et al. |
| 8,444,628 B2 | 5/2013 | Fangrow, Jr. |
| 8,454,579 B2 | 6/2013 | Fangrow, Jr. |
| 8,529,524 B2 | 9/2013 | Newton et al. |
| 8,715,222 B2 | 5/2014 | Truitt et al. |
| 8,882,742 B2 | 11/2014 | Dikeman et al. |
| 2001/0049508 A1 | 12/2001 | Fangrow, Jr. |
| 2002/0120333 A1 | 8/2002 | Keogh et al. |
| 2004/0006330 A1 | 1/2004 | Fangrow, Jr. |
| 2004/0201216 A1 | 10/2004 | Segal et al. |
| 2005/0020981 A1 | 1/2005 | Kurth |
| 2005/0059952 A1 | 3/2005 | Giuliano et al. |
| 2005/0121638 A1 | 6/2005 | Doyle |
| 2005/0222541 A1 | 10/2005 | Lopez et al. |
| 2006/0004331 A1 | 1/2006 | Fangrow, Jr. |
| 2006/0161115 A1 | 7/2006 | Fangrow, Jr. |
| 2006/0200088 A1 | 9/2006 | Lopez |
| 2006/0200089 A1 | 9/2006 | Lopez et al. |
| 2006/0200090 A1 | 9/2006 | Lopez et al. |
| 2006/0206061 A1 | 9/2006 | Lopez et al. |
| 2006/0211997 A1 | 9/2006 | Fangrow, Jr. |
| 2006/0211998 A1 | 9/2006 | Fangrow, Jr. |
| 2006/0211999 A1 | 9/2006 | Fangrow, Jr. |
| 2006/0212001 A1 | 9/2006 | Fangrow, Jr. |
| 2006/0212003 A1 | 9/2006 | Fangrow |
| 2006/0212006 A1 | 9/2006 | Fangrow, Jr. |
| 2006/0224127 A1 | 10/2006 | Fangrow, Jr. |
| 2006/0264842 A1 | 11/2006 | Fangrow, Jr. |
| 2006/0264844 A1 | 11/2006 | Fangrow, Jr. |
| 2006/0264849 A1 | 11/2006 | Lopez et al. |
| 2006/0264909 A1 | 11/2006 | Fangrow, Jr. |
| 2006/0264910 A1 | 11/2006 | Fangrow, Jr. |
| 2006/0270999 A1 | 11/2006 | Fangrow, Jr. |
| 2006/0271016 A1 | 11/2006 | Fangrow, Jr. |
| 2006/0276757 A1 | 12/2006 | Fangrow, Jr. |
| 2006/0276758 A1 | 12/2006 | Fangrow, Jr. |
| 2007/0100284 A1 | 5/2007 | Leinsing et al. |
| 2007/0106205 A1 | 5/2007 | Connell et al. |
| 2007/0112312 A1 | 5/2007 | Fangrow, Jr. |
| 2007/0112313 A1 | 5/2007 | Fangrow, Jr. |
| 2007/0224865 A1 | 9/2007 | Fangrow, Jr. |
| 2007/0225425 A1 | 9/2007 | Nash et al. |
| 2007/0235676 A1 | 10/2007 | Vangsness et al. |
| 2007/0254000 A1 | 11/2007 | Guo et al. |
| 2007/0270756 A1 | 11/2007 | Peppel et al. |
| 2008/0039802 A1 | 2/2008 | Vangsness et al. |
| 2008/0086097 A1 | 4/2008 | Rasmussen et al. |
| 2008/0086099 A1 | 4/2008 | McKinnon et al. |
| 2008/0097407 A1 | 4/2008 | Plishka |
| 2008/0249508 A1 | 10/2008 | Lopez et al. |
| 2009/0209922 A1 | 8/2009 | Boisjoly |
| 2009/0292252 A1 | 11/2009 | Lareau et al. |
| 2010/0036330 A1 | 2/2010 | Plishka et al. |
| 2010/0049157 A1 | 2/2010 | Fangrow |
| 2010/0059702 A1 | 3/2010 | Mansour et al. |
| 2010/0174242 A1 | 7/2010 | Anderson et al. |
| 2010/0249723 A1 | 9/2010 | Fangrow, Jr. |
| 2010/0249724 A1 | 9/2010 | Cote, Sr. et al. |
| 2010/0249725 A1 | 9/2010 | Cote, Sr. et al. |
| 2010/0264343 A1 | 10/2010 | Jeory |
| 2011/0028915 A1 | 2/2011 | Siopes et al. |
| 2011/0046572 A1 | 2/2011 | Fangrow |
| 2012/0109077 A1 | 5/2012 | Ryan |
| 2013/0226099 A1 | 8/2013 | Fangrow, Jr. |
| 2014/0358033 A1 | 12/2014 | Lynn |

FOREIGN PATENT DOCUMENTS

| | | |
|---|---|---|
| CA | 2 175 021 | 11/1996 |
| CH | 636526 | 6/1983 |
| CH | 670955 | 7/1989 |
| DE | 855 319 | 9/1952 |
| DE | 84 25 197 | 9/1985 |
| DE | 37 40 269 | 6/1989 |
| EP | 0 263 789 | 4/1988 |
| EP | 0 309 771 | 4/1989 |
| EP | 0 399 119 | 11/1990 |
| EP | 0 446 463 | 9/1991 |
| GB | 2 000 685 | 1/1979 |
| GB | 2 001 146 | 1/1979 |
| GB | 2 034 185 | 6/1980 |
| WO | WO 92/20736 | 11/1992 |
| WO | WO 99/59672 | 11/1999 |
| WO | WO 99/61093 | 12/1999 |
| WO | WO 03/018104 | 3/2003 |
| WO | WO 2005/115521 | 8/2005 |
| WO | WO 2006/013433 | 2/2006 |
| WO | WO 2006/062912 | 6/2006 |
| WO | WO 2008/048777 | 4/2008 |

OTHER PUBLICATIONS

U.S. Appl. No. 10/217,213, filed Dec. 16, 1996, Fangrow et al.
Capless Backcheck Valve, dated Sep. 3, 1993.
F.D.A. 510(k) Summary of Safety and Effectiveness, dated Nov. 17, 1997.
Saechtling Tworzywa Sztuczne, WN-T Warszawa, 1999, V edition, pp. 224-225.
PASV Valve Connector Brochure, which appears to be at least as early as Feb. 20, 2001.
Nexus Medical Nexus TKO, appears to contain a date of Mar. 2006.
"Faulding Inc. receives FDA permission to market patented Safe-Connect Valve", dated Dec. 2, 1996.
MicroClave Connector Brochure. The MicroClave was available before Mar. 25, 2008.
MEDI-4955 Liquid Silicone Rubber from NuSil Silicone Technology, dated Dec. 17, 2010.
International Search Report and Written Opinion for PCT/US2005039791, dated May 4, 2006.
International Search Report and Written Opinion for PCT/US07/04347, dated Oct. 26, 2007.
Extended Search Report for Application No. 08014856.2 dated Jan. 26, 2009.

* cited by examiner

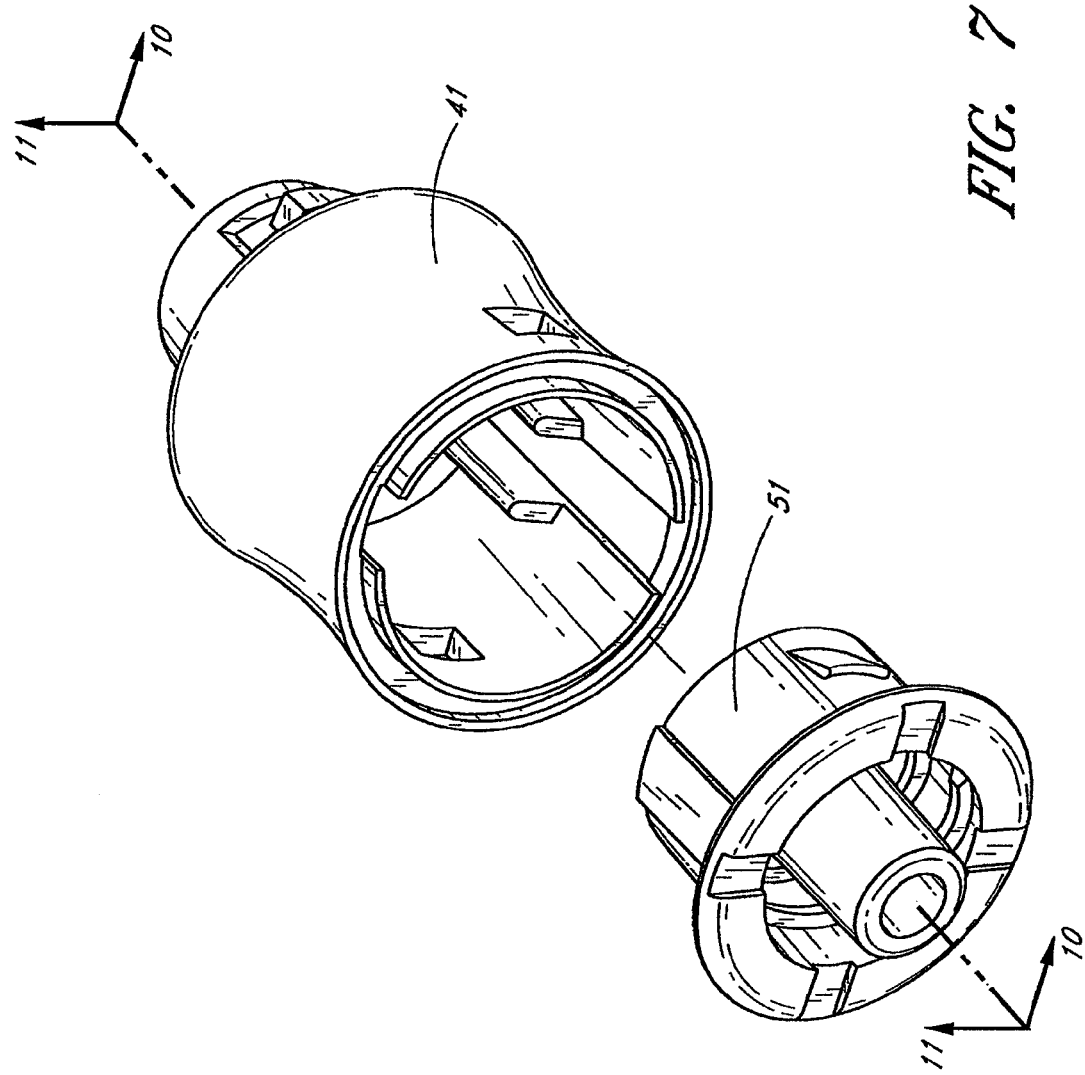

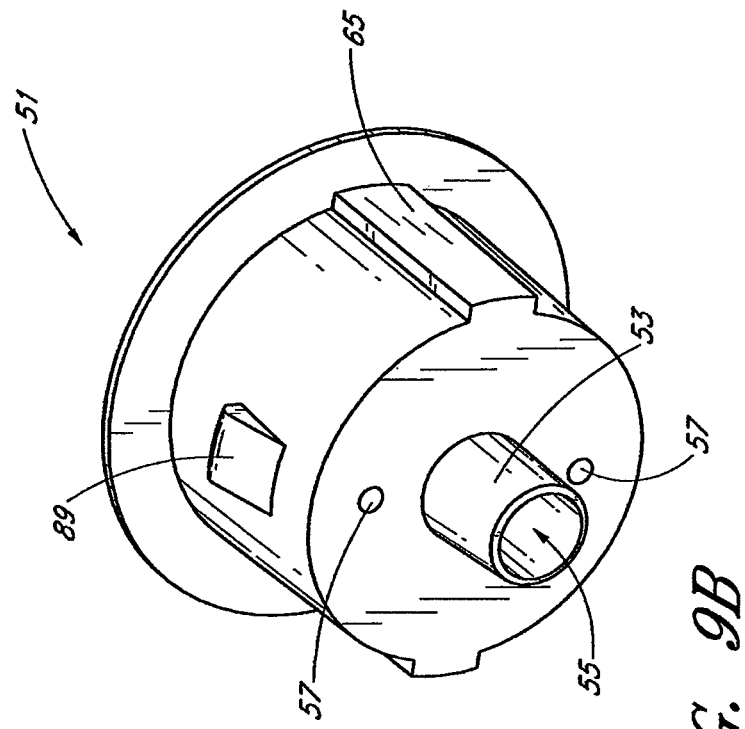
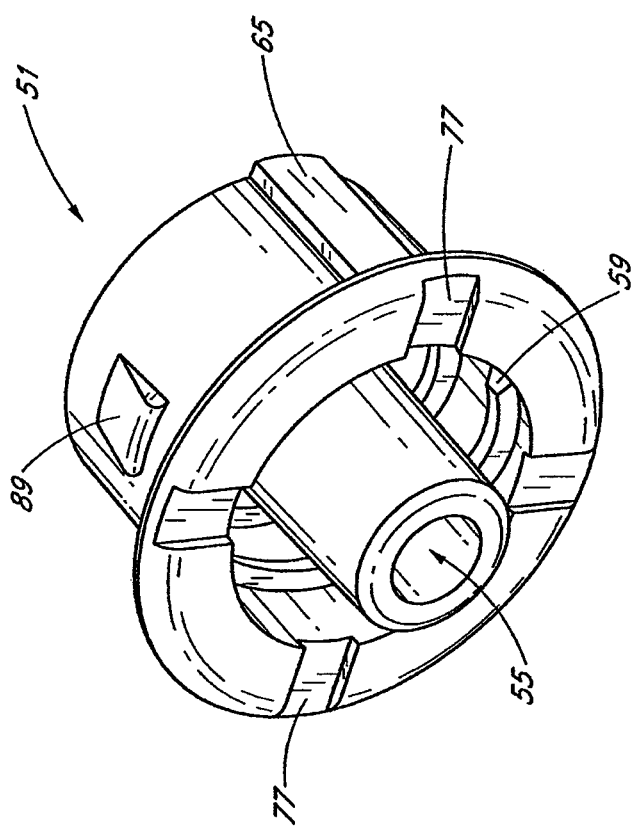
FIG. 9B
FIG. 9A

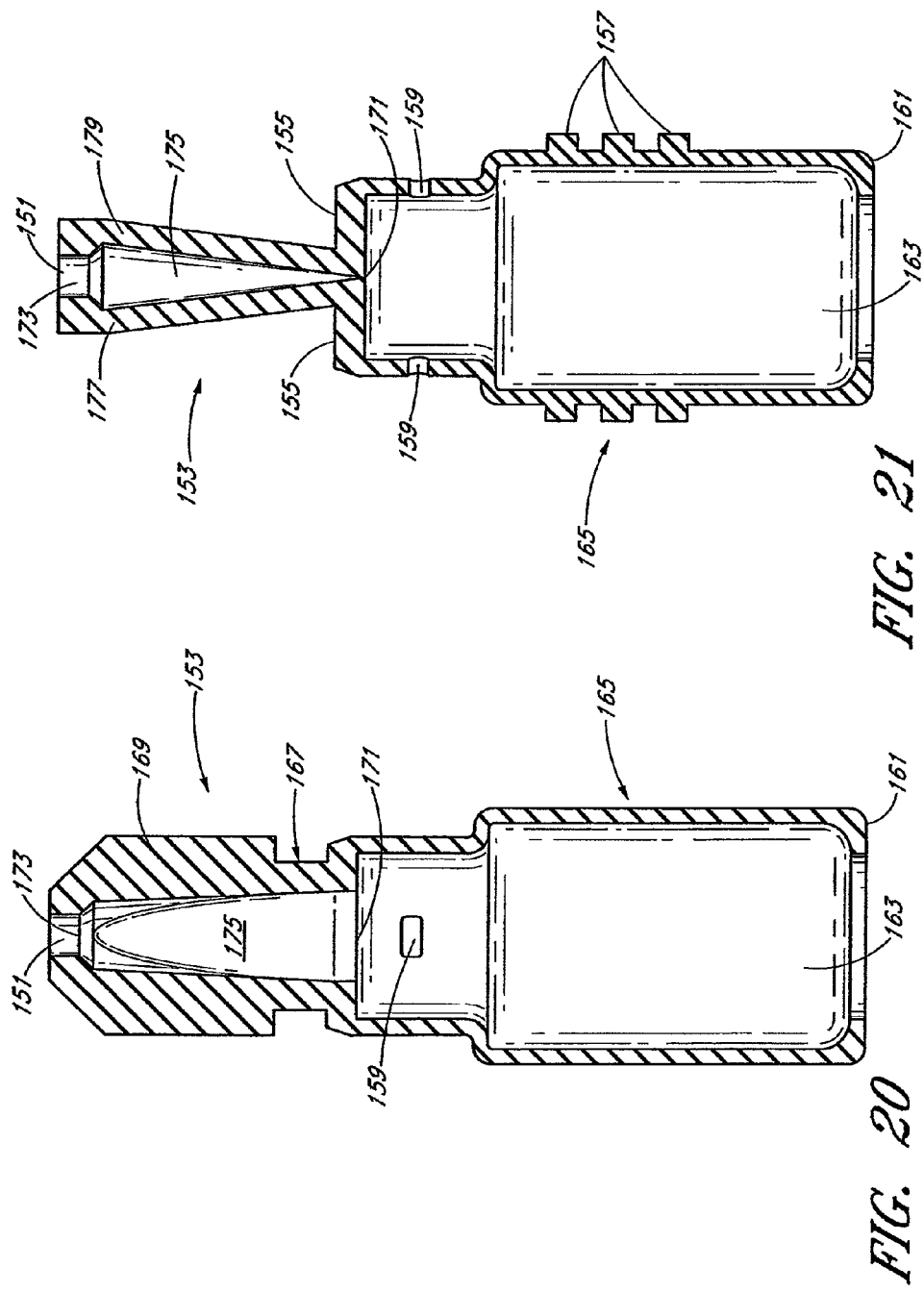

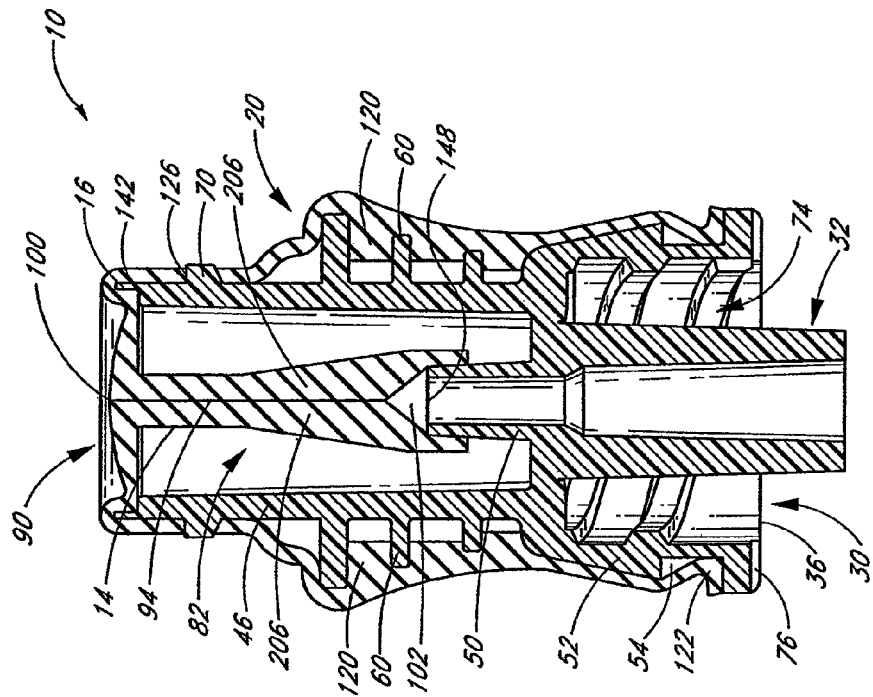
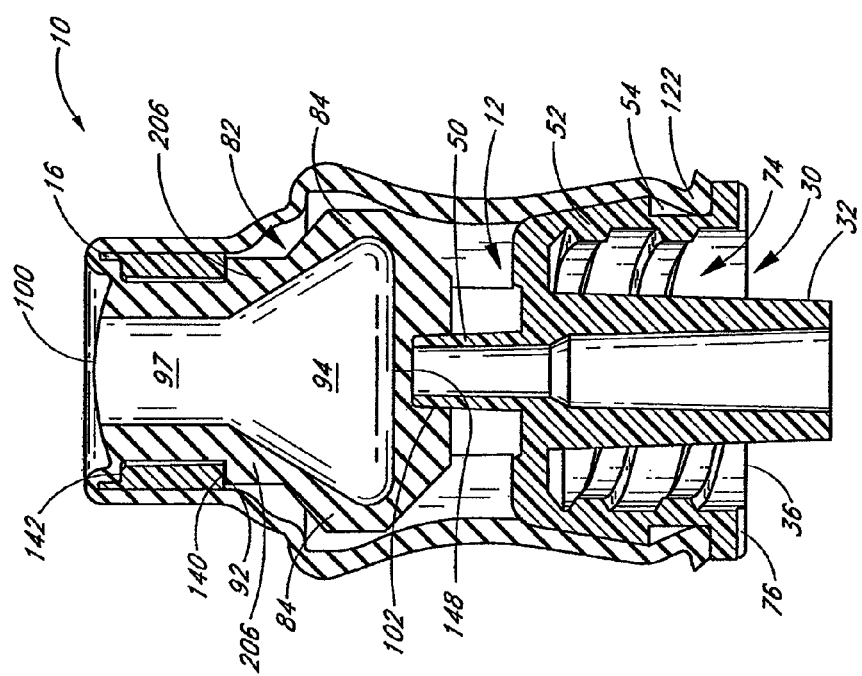
FIG. 24
FIG. 25

MEDICAL CONNECTOR

CROSS-REFERENCE TO RELATED APPLICATIONS

This application is a continuation of U.S. patent application Ser. No. 13/205,463, filed Aug. 8, 2011, which is a continuation of U.S. patent application Ser. No. 12/917,412, filed Nov. 1, 2010, which is a continuation of U.S. patent application Ser. No. 11/417,675, filed May 3, 2006, now U.S. Pat. No. 7,824,393, which is a continuation of Ser. No. 11/267,822, filed Nov. 4, 2005, which claims the benefit of U.S. Provisional Application No. 60/625,644, filed on Nov. 5, 2004, and U.S. Provisional Application No. 60/654,250, filed on Feb. 18, 2005, the entireties of which are hereby incorporated by reference and made a part of this specification for all that they disclose.

BACKGROUND OF THE INVENTIONS

1. Field of the Invention

The inventions disclosed herein relate in general to the field of medical connectors, and in particular to needle-less medical connectors.

2. Description of the Related Art

The manipulation of fluids for parenteral administration in hospitals and medical settings routinely involves the use of connectors for selectively facilitating the movement of fluids to or from patients. For example, a connector may be attached to a catheter that leads to a tip positioned within a patient, and various connectors may be attached to one or more tubes and medical implements to control the fluid flow to or from the patient.

Needle-less connectors are typically structured so that a medical implement without a needle can be selectively connected to such a connector for providing fluid flow between a patient and a fluid source or receptacle. When the medical implement is removed, the connector closes, effectively sealing the catheter connected to the patient without requiring multiple injections to the patient and without exposing health care professionals to the risk of inadvertent needle sticks. The medical implement used with the connector may be a tube or other medical device such as a conduit, syringe, IV set (both peripheral and central lines), piggyback line, or similar component which is adapted for connection to the medical valve.

Many existing medical connectors can be relatively difficult to grasp by health care professionals during use. In most applications, medical connectors are designed to be relatively small to minimize the cost of manufacturing and to minimize the amount of fluid "dead space" inside the connectors. Moreover, most medical connectors include a housing with a hard, smooth outer surface. As a result, it is sometimes uncomfortable for health care professionals to tightly pinch their fingers around the connectors and firmly grasp them during medical procedures in a repetitious manner. Because health care professionals use such connectors very frequently during patient care, enhancements in their ability to effectively grasp the connectors can result in significant improvement in the time and effort required to use them. Additionally, the existing hard-surface medical connectors can be uncomfortable against a patient's skin. This discomfort can become especially pronounced when a patient requires frequent medical attention involving the use of medical connectors, such as hemodialysis.

Additionally, many existing medical connectors at least partially obstruct fluid flow with complex flow passageways including various turns, bends, and corners. These obstructions can result in a fairly low flow rate. The obstructions can also damage blood platelets.

Further, many existing connectors permit some degree of retrograde fluid flow upon the disconnection of these medical devices from the valve. These connectors typically include an internal space through which a fluid may flow from the medical implement to the catheter attached to the connector. When the medical implement is attached to the connector, it typically occupies a portion of this internal valve space, displacing a certain amount of fluid within the connector. When the medical implement is disconnected, a vacuum is created by the removal of the portion of the medical implement from the internal space of the connector, which tends to draw fluid up through the line from the patient toward the connector to fill the space left by the removal of the implement.

This regression of fluid has certain disadvantages. When the connector is attached to a fluid line leading to a patient, retrograde movement of fluid through the line towards the space in the connector has the effect of drawing a small amount of blood away from the patient in the direction of the connector. The blood thus drawn into the catheter may, over time, result in a clog in the catheter near its tip, potentially limiting the effectiveness of the catheter tip.

The likelihood of blood clogging the tip of a catheter is heightened when the inner diameter of the catheter is small. In parenteral applications, such smaller-diameter catheters are used frequently due to their numerous advantages. For example, smaller catheters reduce the trauma and discomfort caused by insertion into a patient. Because these catheters have small lumens, even a small suction force may draw fluid back a comparatively large distance through the catheter toward the connector.

Further, in some existing medical connectors, there are gaps between an internal sealing member and the outer housing of the connector. These gaps may allow bacteria, debris, or disinfectant solution to enter through the opening into the interior of the connector and potentially reach the flow of fluid to or from the patient.

SUMMARY OF THE INVENTIONS

Certain embodiments of the present invention provide a soft-grip medical connector comprising a housing with an upstream end, a downstream end, a lumen extending through a central portion of the housing, and a flexible member. In some embodiments, the flexible member has a valve portion integrally formed with a gripping portion. The valve portion is positioned within a portion of the housing. The valve portion is configured to control a flow of fluid through the housing lumen. The gripping portion covers at least a portion of an outer surface of the housing.

In some embodiments, a medical fluid connector comprises a cylindrical body, a valve portion, and a sleeve portion. The cylindrical body has an outer wall with a plurality of flanges extending radially therefrom and a lumen extending through a portion thereof. The valve portion provides a closeable seal between a first end and a second end of the cylindrical body. The sleeve portion can be unitarily formed with the valve portion and can surround a substantial portion of an outer surface of the cylindrical body.

Methods of forming a gripping and/or sealing portion of a medical device are also provided. In some embodiments, a method comprises injecting an uncured material into a mold, thereby molding a first preform from a substantially flexible material. The preform is removed from the preform mold, and a second preform is molded (though not necessarily in the same mold as the first). The first preform and the second preform are then inserted into a final mold, and an uncured material is injected into the final mold in order to over-mold the first and second pre-forms into a final structure having a valve member and a sleeve portion extending from the valve member.

Methods of making a medical fluid connector are also provided. In some embodiments, the methods comprise the steps of forming a valve member with a sleeve extending therefrom, the valve and sleeve being integrally formed of a substantially flexible material and forming a relatively rigid housing. A portion of the valve member is inserted into a cavity of the housing such that the sleeve extends from the housing member. The sleeve is then inverted to cover or surround at least a portion of an outer surface of the housing member.

In embodiments of a method of using a soft-grip connector, the downstream end is connected to a first medical implement such as a catheter. A second medical implement is inserted into an opening in the upstream end of the connector. Upon introduction of the second medical implement into the connector, in certain embodiments, the valve member expands, creating a larger internal volume. Fluid from the second medical implement is permitted to flow into the valve member. In some embodiments, this introduction of fluid causes further expansion of the volume inside the valve member, and as the fluid flow diminishes or stops, the inside volume of the valve member contracts.

As the second medical implement is withdrawn from the connector, the internal volume of the valve member also decreases. In some embodiments, the valve member can rapidly return to its original state (i.e., before insertion of the second medical implement). A region inside of the valve member near the upstream end is narrower than a region near the downstream end to impede the flow of fluid in the upstream direction and encourage the flow of fluid in the downstream direction. In this way, fluid inside the connector is forced toward the downstream end of the connector in the direction of the patient, creating a positive flow effect and minimizing regression of fluid back into the valve. Various configurations of positive-flow valves are disclosed in U.S. Pat. No. 6,695,817 and U.S. Patent Application Publication No. 2004/0006330, owned by ICU Medical, Inc., and such documents are incorporated herein by reference and form a part of this specification for all that they disclose.

In many embodiments, the connector is small yet easily grippable. The outer sleeve can be made, for example, of silicone rubber, which creates a desirable degree of anti-slip friction against standard rubber gloves worn by health care professionals. In some embodiments, the contours of the connector in the region near the upstream end are generally smooth and seamless due to the integral formation of the flexible outer sleeve and the valve member. In this configuration, it is less likely that bacteria or other debris will gather in areas where fluid flow passes through to the patient and it is easier and more effective to swab such areas with antiseptic. The integral formation of the valve member and outer sleeve also simplifies, and increases the cost-effectiveness, of the manufacturing processes.

BRIEF DESCRIPTION OF DRAWINGS

Having thus summarized the general nature of the invention, certain preferred embodiments and modifications thereof will become apparent to those skilled in the art from the detailed description herein having reference to the figures that follow, of which:

FIG. 7 is an exploded perspective view of another embodiment of housing member of a soft-grip medical connector;

FIG. 9A is a perspective view of a second housing portion of FIG. 7;

FIG. 9B is a perspective view of the second housing portion of FIG. 9A from a reverse angle;

FIG. 20 is a cross-sectional view of the flexible member of FIG. 19, taken through line 20-20;

FIG. 21 is a cross-sectional view of the flexible member of FIG. 19, taken through line 21-21;

FIG. 24 is a cross-sectional view of an assembled soft-grip medical connector;

FIG. 25 is a cross-sectional view of a soft-grip medical connector taken at about 90° relative to the cross-section of FIG. 24;

DETAILED DESCRIPTION OF THE PREFERRED EMBODIMENTS

With reference to the attached figures, certain embodiments and examples of soft-grip medical connectors will now be described. Although certain embodiments and examples of a soft-grip connector are shown and described as including positive-flow valves, certain aspects and advantages of the systems and methods described herein can be advantageously applied to numerous other fluid connector designs including those without positive-flow characteristics.

Figure 1:
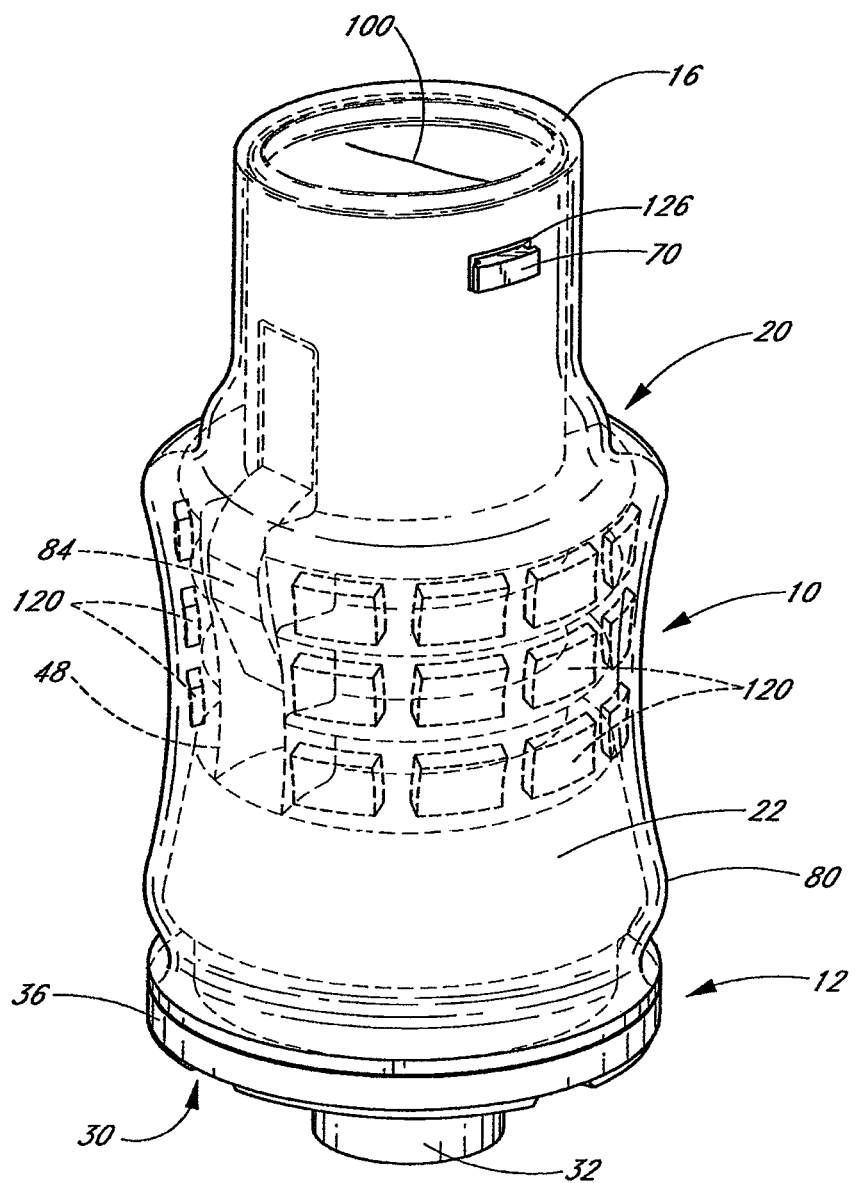
FIG. 1 is a perspective view of one embodiment of a soft-grip medical connector including an outer sleeve surrounding a housing member.

Referring now to FIG. 1, the illustrated embodiment of a medical connector 10 comprises a substantially rigid housing 12 with a flexible member 80 that has been stretched over the outer surface of the housing 12 to provide a soft, grippable outer surface 22. A slit opening 100 is formed at an upstream end 16 of the flexible member 80. The upstream end of the flexible member 80 surrounding the housing 12 provides a surface that is easily cleaned, and is substantially free from cavities or recesses in which contaminants may collect. While as illustrated, the upstream end of the flexible member 80 surrounds the entire circumference of the housing 12, it is contemplated that in other embodiments, the upstream end of the flexible member may circumferentially surround substantially all of the housing 12, or can circumferentially surround a portion of the housing 12 such as approximately three-quarters, approximately one-half, or less. In other embodiments, the flexible member 80 can be segmented to surround multiple portions of the housing 12. For example, the flexible member 80 can have one or more openings or perforations that expose a portion of the underlying housing 12 beneath the flexible member 80, and/or the portions of the flexible member 80 on the outside of the housing 12 can be made of strips or bands that contact the housing 12. The outer surface of the flexible member 80 can cover internal portions of the flexible member 80, such as lateral extensions 84 (discussed in further detail below), to prevent interference with those portions during use, thereby providing for more consistent functionality of the flexible member 80.

Referring now to FIGS. 2-11, embodiments of a housing 12 are described. FIGS. 2-6 depict one embodiment of a housing 12 for use in a soft-grip medical connector. FIGS. 7-11 depict another embodiment of a housing for use in a soft-grip medical connector. Many other embodiments can also be formed by using or combining one or more features of the disclosed embodiments.

With reference to the housing depicted in FIGS. 2-6, the housing 12 comprises an upper cavity 42 for receiving a flexible member 80, and interfaces 16, 30 for joining the connector to a variety of medical devices. An upper housing 40 generally comprises a cylindrical wall 44 having longitudinal slots 46 positioned on opposite sides, e.g., oriented at about 180° relative to one another. At a lower end, the upper housing 40 joins a base member 48 which comprises a lower Luer connector 30 (see, e.g., FIGS. 5 and 6). During storage and shipping of a sterilized connector 10, a protective cap (not shown) can be attached to the lower Luer connector 30 to maintain its sterility before use. The cap is generally removed by a health care professional immediately before connecting the lower Luer connector 30 to a medical implement.

As illustrated, embodiments of a housing member 12 can also include a plurality of ring sections 60 extending radially outwards from the outer surface of the cylindrical wall 44 of the upper housing 40. In some embodiments, the rings 60 are progressively smaller in diameter from top 60a to bottom 60c. In still other embodiments, the number, size, and configuration of the rings 60 can be modified in many other ways.

Figure 23:
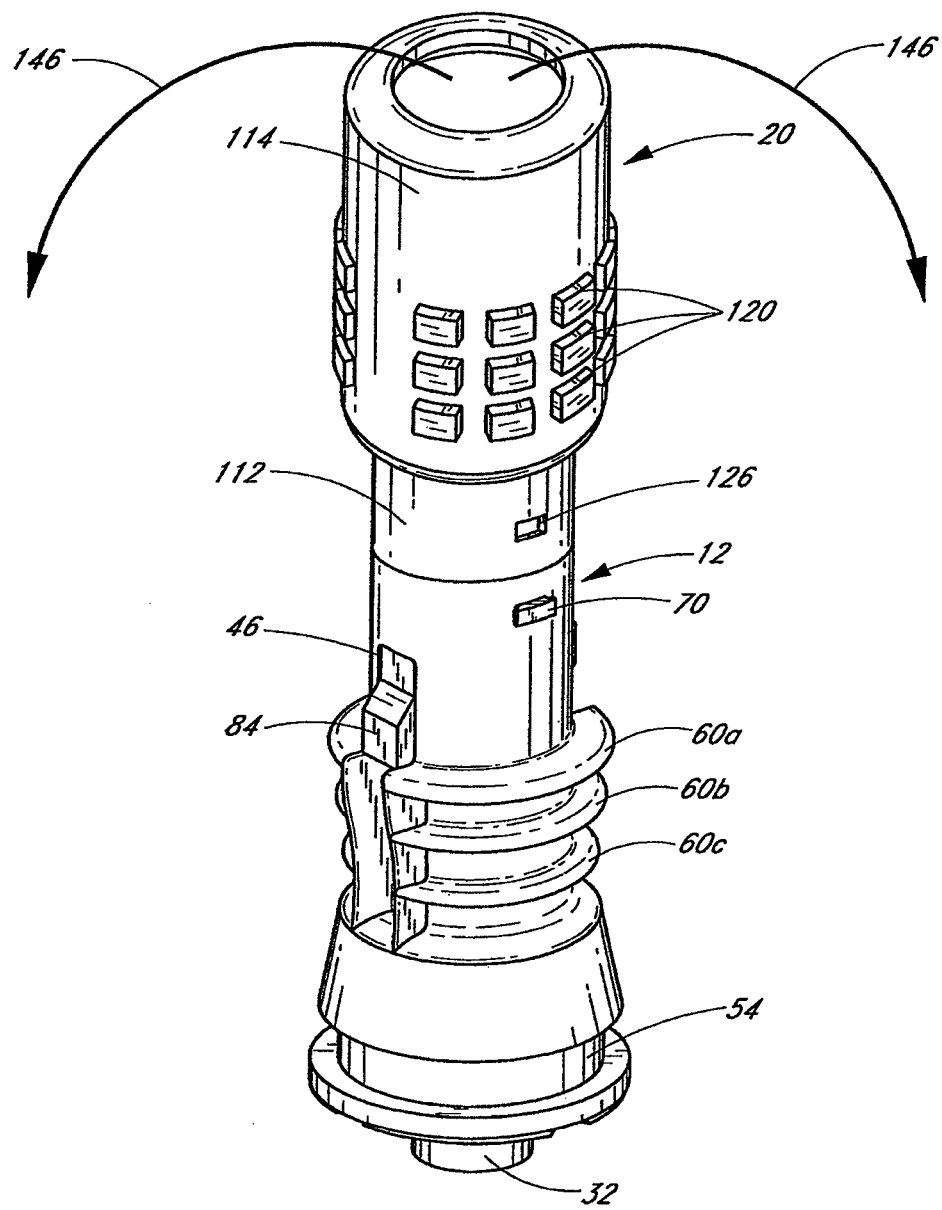
FIG. 23 is a perspective view illustrating the sleeve of the flexible member adjacent to the housing member, with the valve member of the flexible member inserted into the housing member.

Flanges 62 can also be provided at the intersections between the rings 60 and the slots 46. The flanges 62 prevent lateral extensions 84 of the flexible member 80 (see, e.g., FIG. 23), when inserted into the upper housing 40, from snagging or catching on the edges of the rings 60 at the points where such rings 60 are bisected by the longitudinal slots 46. The rings 60 and flanges 62 are generally configured to retain portions of a sleeve 20 on the flexible member 80, as will be discussed in further detail below.

Figure 6:
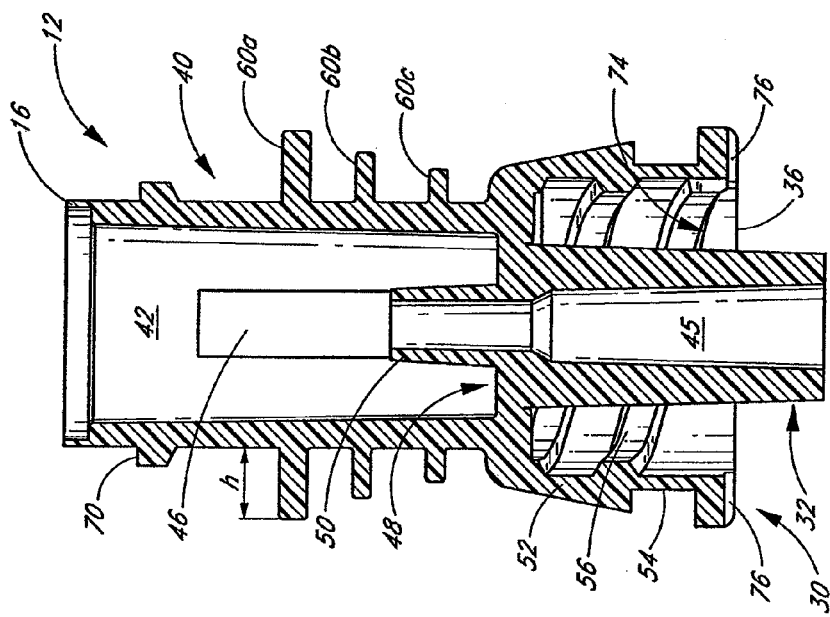
FIG. 6 is a transverse cross-sectional view of the housing member of FIG. 2 taken through line 6-6 (shown in FIG. 3)
Figure 5:
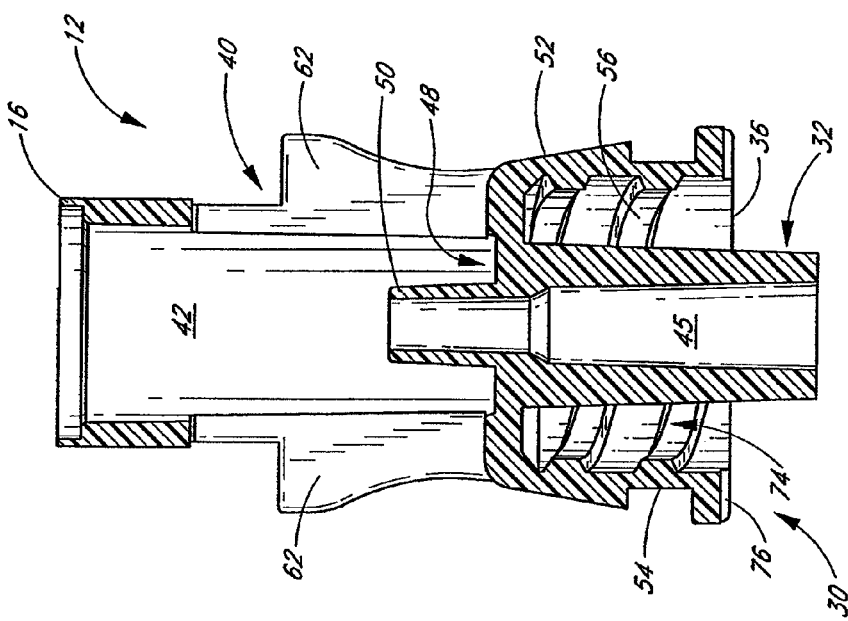
FIG. 5 is a transverse cross-sectional view of the housing member of FIG. 2 taken through line 5-5 (shown in FIG. 3)
Figures 8A, 8B:
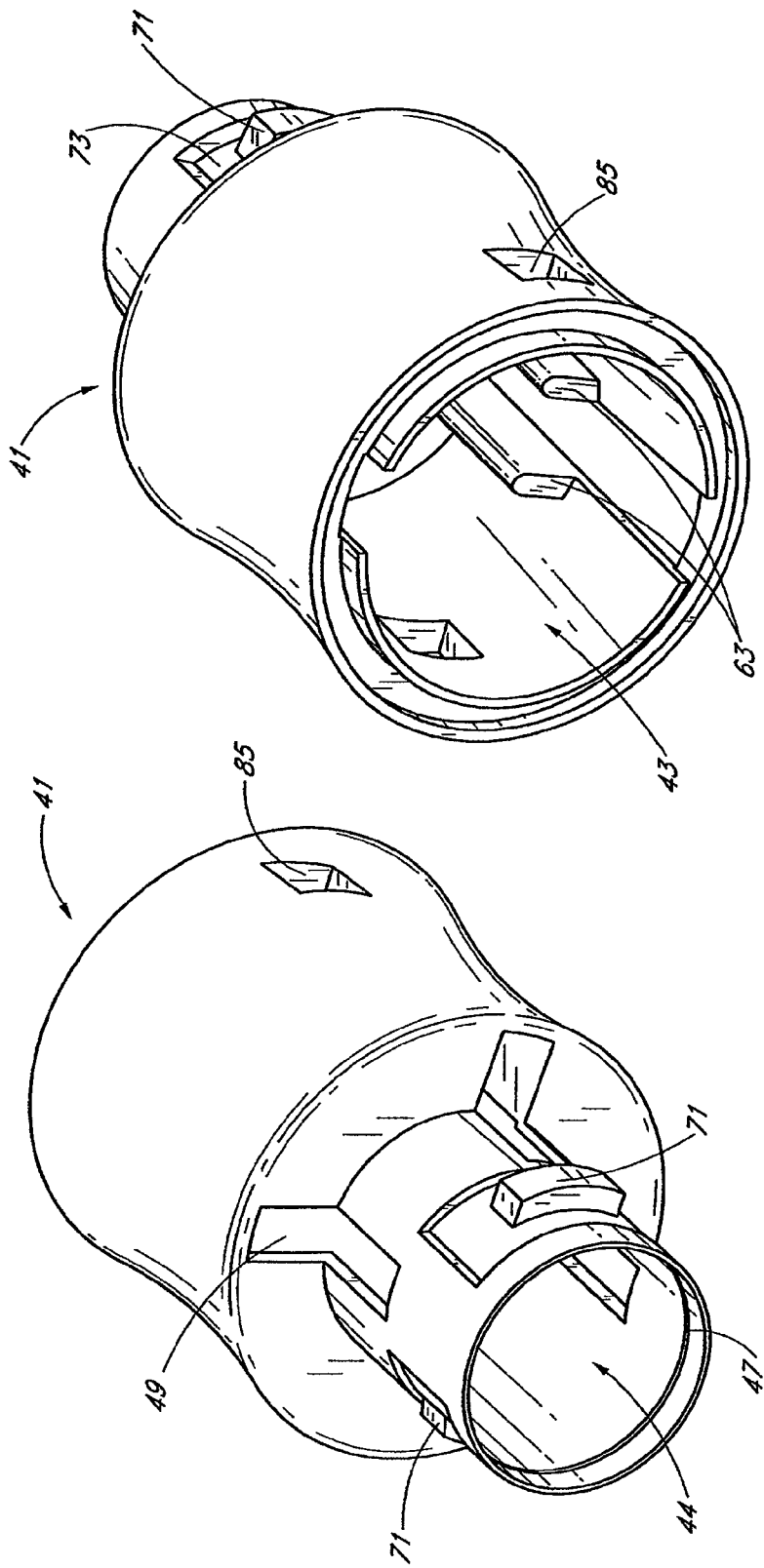
FIG. 8A is a perspective view of a first housing portion of the housing member of the housing member of FIG. 7.
FIG. 8B is a perspective view of the first housing portion of FIG. 8A from a reverse angle.
Figure 11:
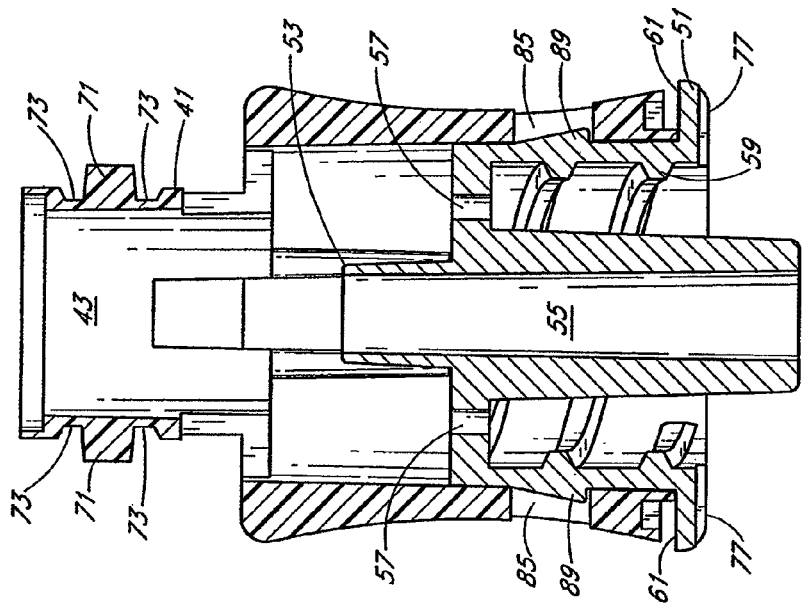
FIG. 11 is a transverse cross-sectional view of the housing member of FIG. 7 taken through line 11-11.
Figure 10:
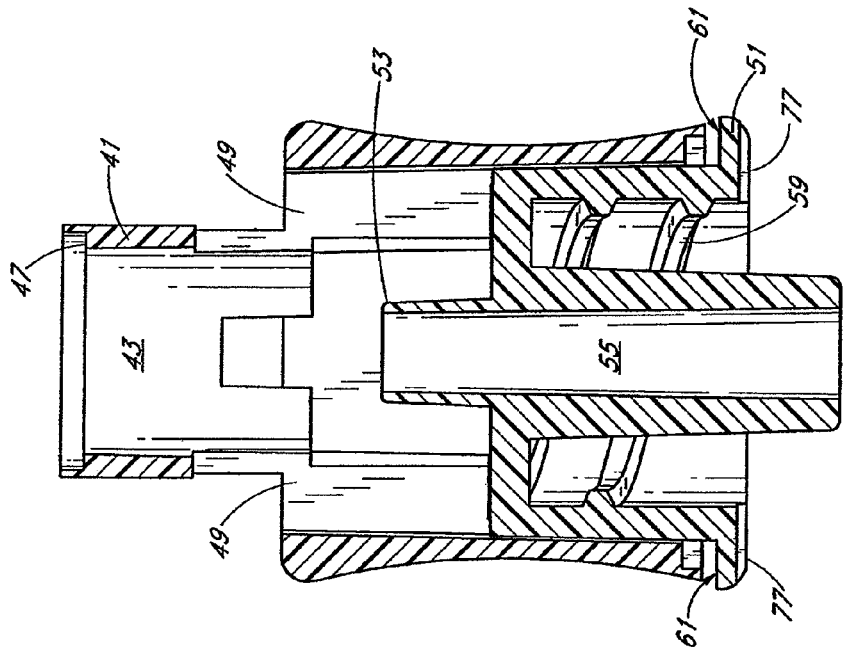
FIG. 10 is a transverse cross-sectional view of the housing member of FIG. 7 taken through line 10-10.

As illustrated in FIGS. 1, 5 and 6, the progressively smaller diameter rings 60 coupled with a frustoconically shaped skirt 52 generally result in an "hourglass" shaped housing. This advantageously assists in providing an easily grippable connector. The smaller-diameter region near the lower end of the upper housing 40 can be grasped between the thumb and index finger of a health care professional. In the region of the rings 60, the progressively larger diameter regions above and below the smaller-diameter region make it less likely that the person's grip will slide along the outside surface of the connector 10 when other medical implements are attached to it or detached from it. In addition, other gripping surfaces such as bumps, ridges, and other types of indentations or protrusions can be provided on the outside surface of the sleeve 20 in the region where the health care provider's fingers are expected to grasp the connector 10.

The dimensions of the housing 12 preferably allow for a compact connector. Advantageously, a compact connector is relatively low cost as it requires a relatively small amount of material to manufacture. Further, the compactness typically results in a lightweight connector, thus reducing irritation to a patient when a connector is rested on or hanging from the patient for a relatively long duration use. For example, in some embodiments, the housing 12 has a height from an upstream end 16 to a downstream end of a Luer cannula 32 of between about 0.400" and 1.200". In other embodiments, the height of the housing 12 can be between about 0.500" and 1.000". In still other embodiments, the height is less than 1.000". The height of the upper housing 40 from an upstream end 16 to the lower Luer connector 30 is between about 0.500" and 0.750". Preferably, the upper housing 40 comprises approximately three-fourths to four-fifths of the overall height of the housing 12. A Luer cavity 74 has a height extending from the lower end 36 of the housing 12 to a lower surface of the base member 48. In certain embodiments, the height of the Luer cavity is between approximately 0.150" and 0.350". In other embodiments, the height of the Luer cavity is less than approximately 0.400". In a certain embodiment, the height of the Luer cavity is approximately 0.220". Preferably, the height of the Luer cavity 74 corresponds to a length of a Luer connector to be inserted in the Luer cavity 74 such that the Luer connector can be flushly inserted into the Luer cavity 74. Preferably, the height of the Luer cavity 74 comprises from between approximately one-eighth to approximately one-third of the height of the housing 12. In certain embodiments, a Luer cannula 32 extends past the lower end 36 of the housing 12 approximately 0.050" to 0.150". In other embodiments, the Luer cannula 32 extends past the lower end 36 approximately 0.80" to 0.120". In a certain embodiment, the Luer cannula 32 extends past the lower end 36 approximately 0.093". Preferably, the Luer cannula is sized and configured to couple with a Luer connector to be inserted into the Luer cavity 74.

The dimensions of the rings 60 and other housing structures correspond to features of the sleeve 20 as will be further described below. For example, in some embodiments, the cylindrical wall 44 has an outer diameter of between about 0.200" and about 0.300", preferably between about 0.250 and about 0.275, and in one particular embodiment, a diameter of about 0.265. In such embodiments, the upper ring 60a has a height 'h' (i.e. the difference between the outer diameter of the ring and the outer diameter of the cylindrical upper housing) of about 0.110" (±0.02"), the middle ring 60b has a height of about 0.093" (±0.02"), and the lower ring 60c has a height of about 0.073" (±0.02"). Thus, in certain embodiments, the housing 12 includes a generally hourglass-shaped body defined by the cylindrical wall 44 and the rings 60a, 60b, 60c and having a maximum diameter of between about 0.310" and 0.410", preferably between about 0.360" and 0.385", and in one particular embodiment, about 0.375". Other dimensions within and outside of the above ranges can also be used depending on the particular application desired.

Figure 2:
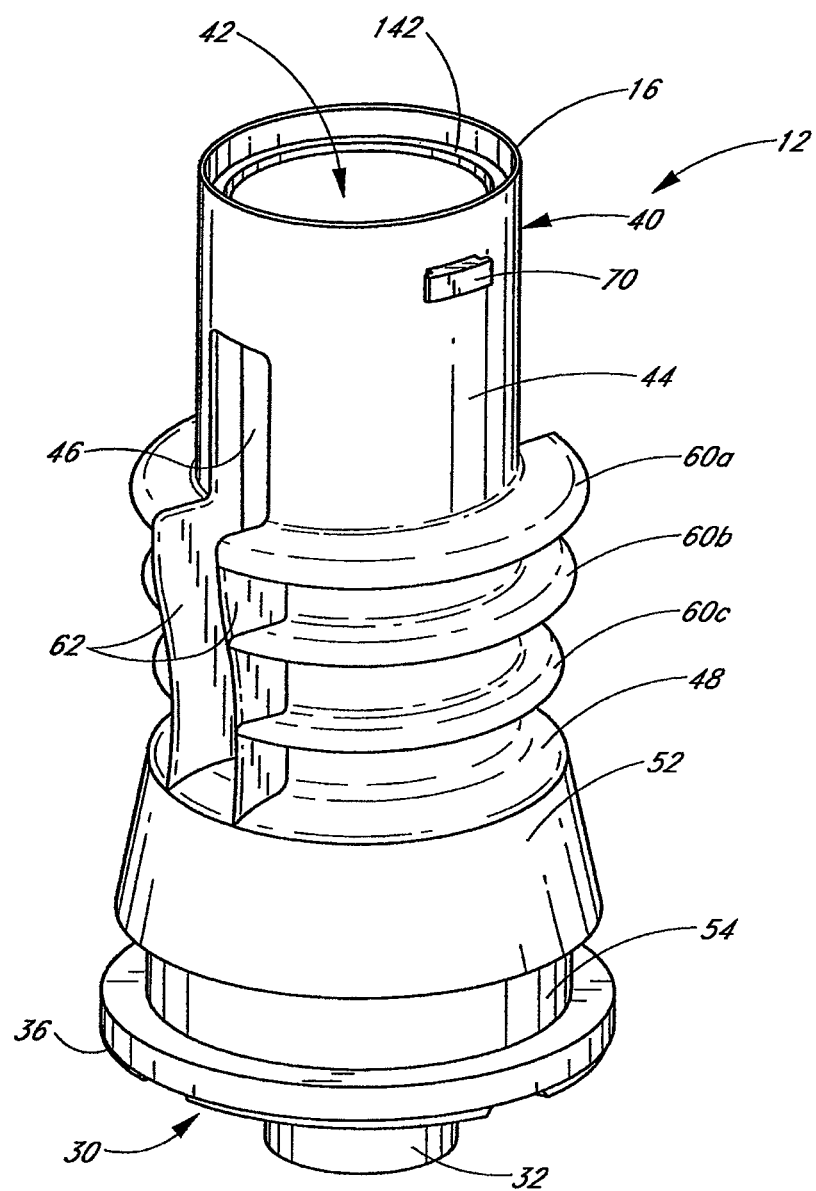
FIG. 2 is a perspective view of one embodiment of a housing member of a soft-grip medical connector.
Figure 4:
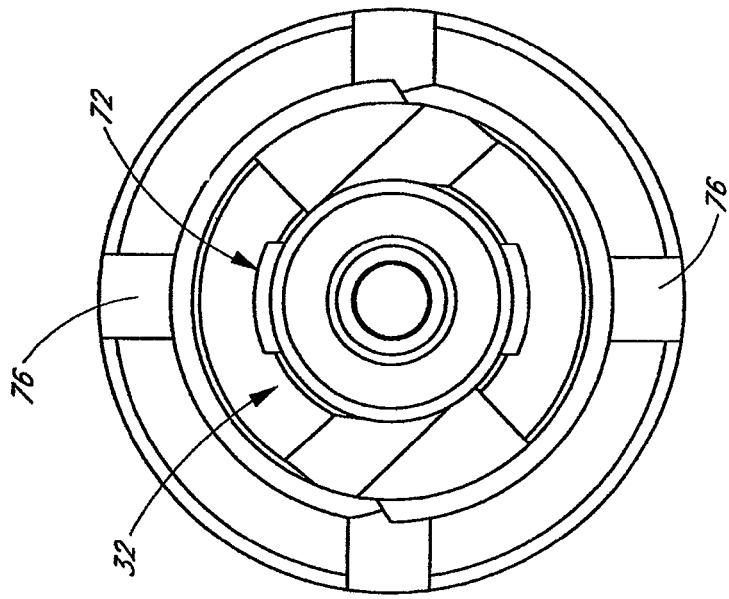
FIG. 4 is a bottom plan view of the housing member of FIG. 2.
Figure 3:
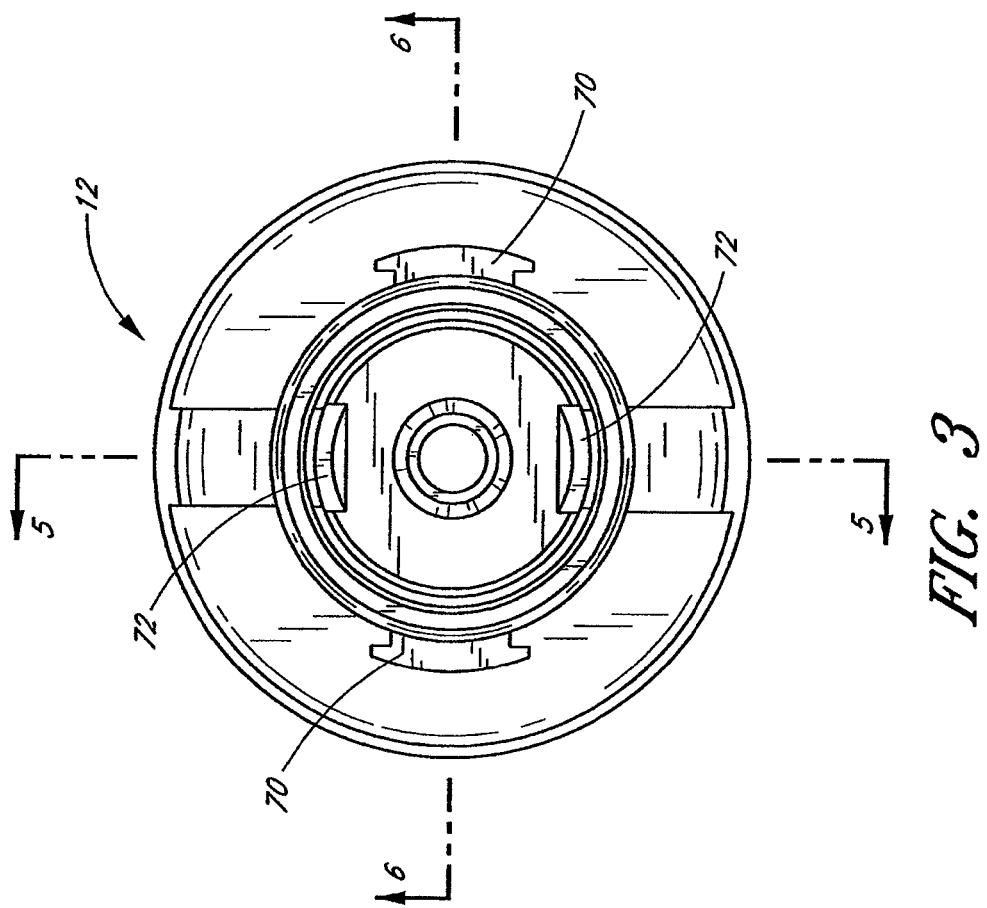
FIG. 3 is a top plan view of the housing member of FIG. 2.

As shown, for example, in FIGS. 1, 2 and 5, the housing 12 can also include protrusions 70 such as lugs for receiving a threaded medical connector such as a Luer connector of a medical device such as a syringe. In the illustrated embodiment, the protrusions 70 lugs are generally rectangular in shape. The lugs can also have substantially rounded or beveled edges so as to prevent damage to the sleeve 20 of the flexible member 80 after it is stretched over the outside of the housing 12, as described in greater detail below. The sleeve 20 can include windows 126 configured to allow the protrusions 70 to protrude through the flexible member 80, while preferably tightly engaging the periphery of the protrusions 70, when the sleeve 12 is inverted (as will be discussed in further detail below). In other embodiments, the protrusions 70 can comprise other shapes and configurations as desired. In some embodiments without windows 126, the protrusions 70 are sized to cooperate with a thickness of the sleeve, such that the protrusions 70 form a lump in the sleeve sufficient to engage a female thread of a Luer connector to be attached to the upstream end 16 of the connector 10.

In some embodiments, the lower housing interface comprises a Luer connector 30 to facilitate joining the connector 10 to medical devices with female Luer connectors. The Luer connector 30 of the housing 12 can comprise a hard cannula 32 extending downwardly from the lower end 36 of the housing 12 to provide a connection with another medical device, such as a catheter hub. Other interfaces and connections can also be used in place of the Luer connector 30, such as Luer slip connections, barbed hose fittings, etc.

As shown in FIGS. 5 and 6, the housing also includes an interior cannula 50 extending into the upper housing cavity 42. The interior cannula 50 comprises a lumen 45 extending through the base member 48 and through the Luer cannula 32 of the lower Luer connector 30. The lower Luer connector 30 also includes a skirt 52 which extends downwards from the base member 48 and typically comprises internal threads 56 or other features for securing the connector 10 to another medical device. The skirt 52 can comprise a taper from a narrower upper portion to a larger-diameter lower portion. In some embodiments, the skirt 52 also includes an incut annular groove 54 around the perimeter of the skirt 52 at a lower portion thereof. This annular groove 54 can be used to retain a portion of the sleeve as will be described in further detail below.

In certain embodiments, it is desirable to provide vents 72 (see FIG. 4) between the upper housing cavity 40 and the cavity 74 defined by the lower Luer skirt 52. Since the outer surfaces of the housing 12 are generally in contact with the sleeve 20 in the final assembly (and, as discussed below in connection with assembly of the medical connector 10, in certain embodiments, the sleeve 20 can cover the entire outer surface, or nearly the entire outer surface, of the housing 12), such ventilation between the upper housing 40 and the cavity 74 is helpful in allowing air, gaseous sterilizing agents or other gases to flow freely into and/or out of the upper housing cavity. This ventilation can be particularly helpful when and as a medical implement is inserted into the slit opening 100 of the connector 10 and the flexible member 80 expands, diminishing the volume between the outer surface of the flexible member 80 and the inner wall of the upper housing 40. The vents 72 may also allow moisture and other liquids to flow freely into and/or out of the upper housing cavity, thus reducing the risk that a volume of liquid could become trapped in the upper housing 40 and restrict expansion of the flexible member 80, provide a hospitable environment for the growth of unwanted bacteria, or otherwise adversely affect the operation of the medical connector 10. Without venting, such insertion of the medical implement could be met with resistance, creating undue wear on the flexible member 80 and requiring additional effort to use the connector 10. Similarly, recessed vents 76 can be provided in the lower end 36 of the Luer skirt 52 to allow air or other gases to escape from the interior of the Luer cavity 74 while the connector 10 is attached to another medical device. Additionally, the recessed vents 76 allow air or other ambient gases to enter the Luer cavity 74 while the other medical device is removed from the medical connector 10 such that the medical device does not become vacuum locked to the medical connector 10. The recessed vents 76 also allow water, cleaning or disinfecting solutions, or other liquids to escape the Luer cavity 74 while the medical connector 10 is connected to another medical device. In some embodiments, it can be desirable to provide ventilation holes in the sleeve 20 itself.

With reference to FIGS. 7-11, in certain embodiments, the soft-grip medical connector comprises a housing formed of more than one housing portion. In the illustrated embodiments, the housing is formed of a first housing portion 41 and a second housing portion 51. FIG. 7 illustrates an exploded perspective view of a two-piece housing. FIGS. 8A and 8B are perspective views of the first housing portion 41, and FIGS. 9A and 9B are perspective views of the second housing portion 51.

In some embodiments, a two-piece housing may include many or all of the structural features of the housing illustrated in FIGS. 2-6 and described above. In other embodiments, the housing may include more than two pieces. The two-piece housing illustrated in FIGS. 7-11 includes protruding lugs 71 for receiving a threaded medical connector such as a Luer connector of a medical device such as a syringe. The first housing portion 41 also includes longitudinal slots 49 oriented at approximately 180° relative to each other. In some embodiments, a different number of slots or ridges can be provided and the slots or ridges can be of sizes or positions. The first housing portion 41 defines an upper cavity 43 for receiving a flexible member 80. The second housing portion 51 includes a threaded Luer cavity 59. Additionally, the second housing portion may include recessed vents 77 in the lower surface of the Luer cavity 59. The second housing portion includes an interior cannula 53 comprising a lumen 55 extending through the second housing portion 51. Moreover, the second housing portion may include vents 57 between the first housing portion 41 and the second housing portion 51. Further, it is contemplated that a two-piece housing can have dimensions corresponding to the ranges discussed above with respect to the embodiments of one-piece housing 12 illustrated in FIGS. 2-6. Therefore, in certain embodiments of medical connector, a two-piece housing could be used interchangeably with a one-piece housing.

The two piece housing illustrated in FIGS. 7-11 also can also include additional features. For example, the two-piece housing can include various alignment and coupling features to ease assembly of the first housing portion 41 with the second housing portion 51 into a complete housing. For alignment, the second housing portion may include at least one ridge 65, and the first housing portion at least one corresponding recess 63. As illustrated in FIG. 7, the ridge 65 and sidewall 63 are configured to align the first housing portion 41 in a desired orientation with the second housing portion 51 during assembly of the housing. To retain the housing in a coupled orientation, the first housing portion 41 includes at least one tab 89, and the second housing portion 51 includes at least one recess 85 configured to receive the tab 89. As illustrated, the tab 89 has a wedge-shaped profile including a lead-in surface and an interference surface such that the lead in surface facilitates insertion of the tab 89 into the recess and the interference surface prevents withdrawal of the tab 89 from the recess 85. While described herein and illustrated in terms of certain structures, it is contemplated that other alignment and coupling features can be used to couple the two housing portions 41, 51.

In the housing illustrated in FIGS. 7-11, the assembly of first and second housing portions 41, 51 results in a space 61 between the housing portions 41, 51. Advantageously, the space 61 may be sized and configured to retain an end of a flexible member 81. Thus, in such a configuration, the rings 60 used in one-piece housing 12 (FIGS. 2-6) need not be present on a two-piece housing to reduce slippage of the housing relative to a flexible member 80 disposed thereon. In order to further reduce slippage of a flexible member 80 relative to the housing, an area of the first housing portion adjacent the lugs 71 may include a recess 73 to receive an adhesive such that the flexible member 80 may be adhered to the housing. The adhesive and housing materials should be chosen to be compatible. For example, a silicone-based adhesive may be applied to adhere a glass-reinforced thermoplastic polyester resin housing to a silicone rubber sleeve 20. In addition to the slippage reduction noted above, the two-piece housing depicted in FIGS. 7-11 may be manufactured quickly and inexpensively in two separate one-step molding processes as opposed to a two-step molding process required to manufacture a more complex single-piece housing.

Figure 12:
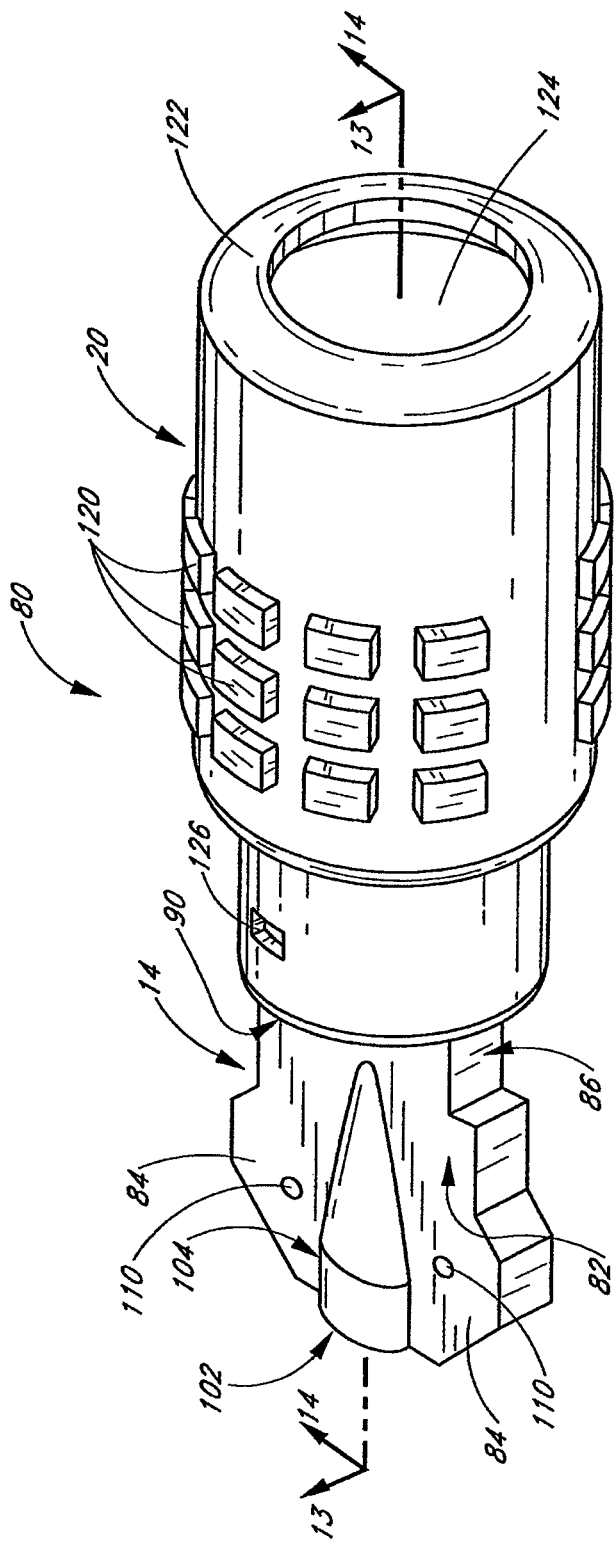
FIG. 12 is a perspective view of a flexible member including a valve member and a sleeve connected to the valve member.
Figure 13:
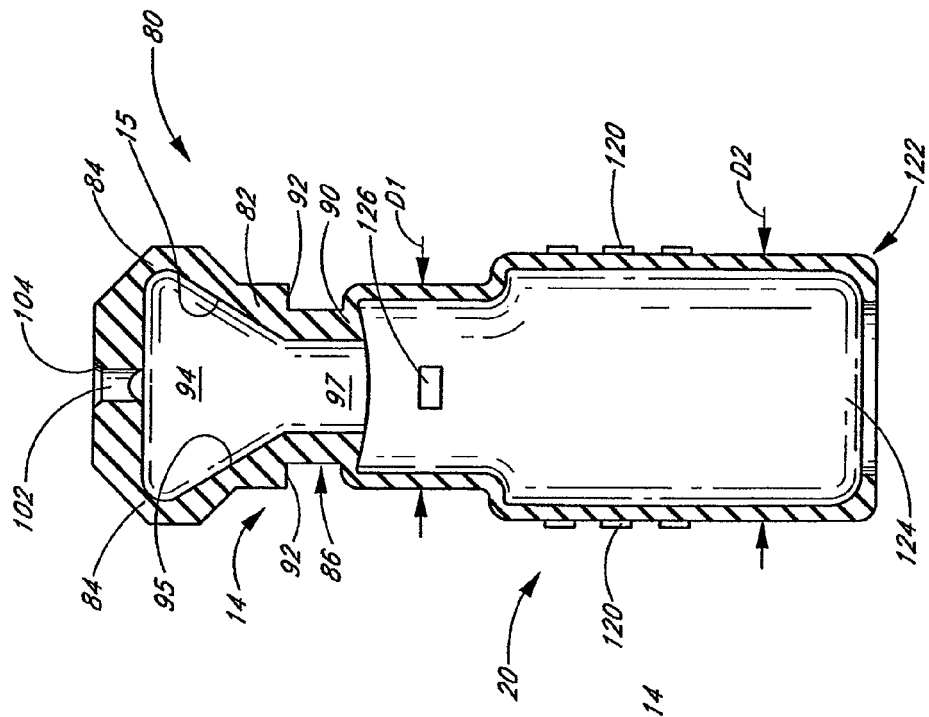
FIG. 13 is a cross-sectional view of the connector of FIG. 12, taken through line 13-13.
Figure 14:
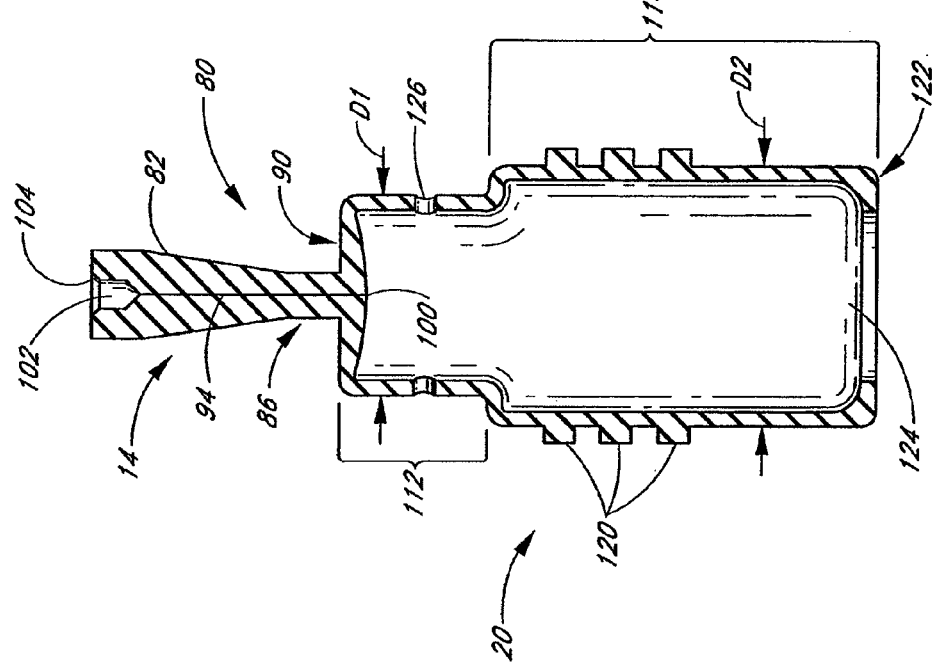
FIG. 14 is a cross-sectional view of the flexible member of FIG. 12, taken through line 14-14.

As illustrated in FIGS. 12-14, in some embodiments, the valve member 14 and sleeve 20 are unitarily formed in a flexible member 80. The flexible member 80 is shown removed from the housing 12 to emphasize details. Some embodiments of valve member 14 have a seal body 82 which may take the form of a slab-like structure that is relatively thin in one dimension and relatively wide in another. The valve member 14 is configured to selectively seal the connector. The term "seal" is used herein for convenience to refer to structures capable of impeding fluid flow but does not necessarily denote that such structures, either alone or in combination with other structures, form a barrier that is completely impermeable to fluid flow. In some embodiments, the body 82 comprises lateral extensions 84 extending laterally from the body 82. The body 82 can also comprise a flat, generally rectangular neck 86 and a transverse flange 90. In some embodiments, the sleeve 20 is integrally formed with the flange 90 and extends axially away from the seal body 82.

The neck 86 is positioned between first and second lateral extensions 84, which each have shoulders 92 comprising those portions of the lateral extensions nearest the flange 90. The body 82, neck 86, flange 90, and sleeve 20 can thus form an integral unit. The body 82 is generally configured to include a narrow passageway or slit 94 extending through the body 82. The slit 94 generally extends through the body 82 including the neck 86 and the flange 90. In FIG. 14, the vertical cross-sectional plane of the drawings coincides with the vertical plane of the slit 94, revealing the wide horizontal width of the slit 94 on the downstream end in this dimension. The slit 94 also includes tapering sides 95, and a narrower neck 97. FIG. 13 demonstrates the narrowness of the slit 94 in a cross-sectional plan orthogonal to the cross-sectional plane of FIG. 14.

As will be described more fully below, the valve member 14 is inserted into the cavity 42 of the housing 12. The slit 94 is generally sized and shaped to permit insertion of a cannula of a syringe or other medical device therein. The connector can be adapted to receive an ANSI standard syringe Luer tip. In some embodiments, the slit 94 is configured to assist in producing a valve that exhibits positive flow characteristics.

The slit 94 extends from the slit opening 100 in the flange 90 to a lead lumen 102 formed in a the downstream end of the body 82 opposite the flange 90. In some embodiments, the lead lumen 102 can be substantially cylindrical and centered about an axis that is substantially parallel to or collinear with the longitudinal axis of the valve member 14. The lead lumen 102 can also be provided with an enlarged external diameter section 104 (e.g. see FIG. 14) configured to aid in positioning the lead lumen 102 over the interior cannula 50 of the housing 12 and to avoid unduly diminishing the cross-sectional area for fluid flow after the flexible member 80 is so positioned.

As illustrated in FIG. 13, some embodiments of the slit 94 can be substantially planar and have a very small thickness in the undisturbed state (i.e. when a syringe cannula is not inserted into the valve member 14). The slit 94 thus forms a selectively restricted fluid flow path from the slit opening 100 to the lead lumen 102. Preferably, the flow path permits either no fluid, or a clinically negligible amount of fluid, to pass through the flexible member 80 under the various standard fluid pressure conditions of patient treatment.

The slit 94 is generally configured to provide a sealable fluid pathway between the slit opening 100 and the lead lumen 102. In some embodiments, the slit 94 can be configured as shown and described herein or as shown and described in any of the patents and applications incorporated herein by reference. The slit 94 is typically made to have essentially no space between adjacent faces of the slit. Examples of methods for making a suitable seal are described in further detail below.

In the embodiment illustrated in FIG. 12, the lateral extensions 84 generally comprise polygonal, angular shapes, although other suitable shapes can be used in view of particular design objectives. The lateral extensions 84 are generally configured to provide structures that interact with portions of the housing 12 in order to retain the valve member 14 in the housing 12 at a desired orientation. As illustrated in FIG. 12, dimples 110 can be formed in the flat surfaces of the lateral extensions 84. In other embodiments, dimples 110 can be formed on another surface of the valve member 14, and, in still other embodiments, the valve member 14 does not include dimples 110. The dimples 110 can be used for retaining and positioning the valve member 14 and lateral extensions 84 during molding and assembly of the connector as will be further described below.

In the embodiments of FIGS. 13 and 14, a sleeve 20 extends axially from the transverse flange 90 of the valve member 14 to the opposite end of the flexible element 80. The sleeve 20 can comprise a first section 112 with a first diameter D1 substantially corresponding to the diameter of the transverse flange 90, and a second section 114 with a second diameter D2 that is slightly larger. In some embodiments, the length of the first section 112 having the first diameter D1 is approximately equal to a distance between the upstream end 16 of the housing 12, and the upper ring 60a of the housing 12. The second section 114 of the sleeve 20 is typically sized to be approximately the same diameter as, or slightly smaller than, the narrowest portion of the hourglass-shaped housing. Thus, when the sleeve 20 is inverted and stretched to surround the housing 12, the sleeve 20 will preferably cling tightly to the exterior surface of the housing along substantially the entire length of the housing 12.

To retain the sleeve 20 in an inverted position surrounding the housing 12, the sleeve 20 can be provided with retaining structures to engage portions of the housing 12. Such retaining structures can include any of a variety of structures, such as protrusions, ribs, ridges, and constrictions. In the embodiments illustrated in FIGS. 12-14, the sleeve 20 comprises a plurality of protrusions 120. In other embodiments, continuous annular ribs can be used in place of the protrusions. Such annular ribs may tend to buckle when the sleeve is turned inside-out, thus causing ripples and irregularities in the outer surface of the finally assembled device. Thus, rows of protrusions 120 such as those illustrated in FIG. 12 are used in many embodiments to allow the sleeve 20 to lie more smoothly on the outer surface of the housing 12. The rows are generally configured such that adjacent protrusions abut one another without deforming the sleeve 20 when the sleeve 20 is inverted. Each of the protrusions 120 can have many shapes including rectangular, circular, and/or elliptical shapes.

The protrusions 120 can be provided in annular rows generally configured to correspond to the spaces between the rings 60 of the housing 12. The length of each row is generally also sized to allow the protrusions to lie between the linear flanges 62 adjacent the slots 46. In other embodiments, the sleeve protrusions 120 and/or the rings 60 and flanges 62 of the housing 12 can be provided in any pattern of cooperating structures to allow the sleeve 20 to be retained against axial and/or rotational movement relative to the housing 12. For example, in some embodiments, the sleeve 20 further comprises recesses or windows 126 for receiving and surrounding portions of the housing, such as the Luer protrusions 70 (see FIG. 1). In other embodiments, as discussed above with reference to the two-piece housing of FIGS. 7-11, the housing does not have rings 60, so the flexible member need not have protrusions (see FIGS. 16-18).

In the illustrated embodiment, the sleeve 20 comprises a constriction 122 surrounding the opening 124 of the sleeve 20. The constriction 122 generally comprises a section of the sleeve with a reduced diameter as compared to the second section 114. The constriction 122 can be configured to engage a feature on the housing 12 such as the annular groove 54 (see e.g. FIGS. 24 and 25) when the sleeve 20 is inverted over the housing 12. In other embodiments, the constriction 122 can be configured to engage and be retained by a space 61 between a first housing portion 41 and a second housing portion 51 (see FIGS. 10 and 11).

As described previously, some embodiments of a sleeve 20 can be provided with one or more windows 126 to accommodate and surround one or more structures on the housing such as protrusions 70 (also referred to as Luer lugs) or sized to receive a standard Luer connector. In such embodiments, the windows 126 can be molded to include thicker edges to prevent undesirable tearing of the sleeve material during assembly or use.

Moreover, as previously described, in some embodiments the sleeve 20 is not formed integrally with the valve member 14. The sleeve 20 can also be formed by adhering, coating, or otherwise providing an outside surface on the housing 12 with a suitable gripping region (instead of mechanically stretching a separately formed sleeve member over the outside surface of the housing 12). The sleeve 20 can also be formed as a band or clip that extends around only the portion of the housing 12 where the fingers of the health care provider are expected to grip the connector 10. Also, in certain embodiments, the connector 10 may be constructed without a sleeve 20.

Figure 16:
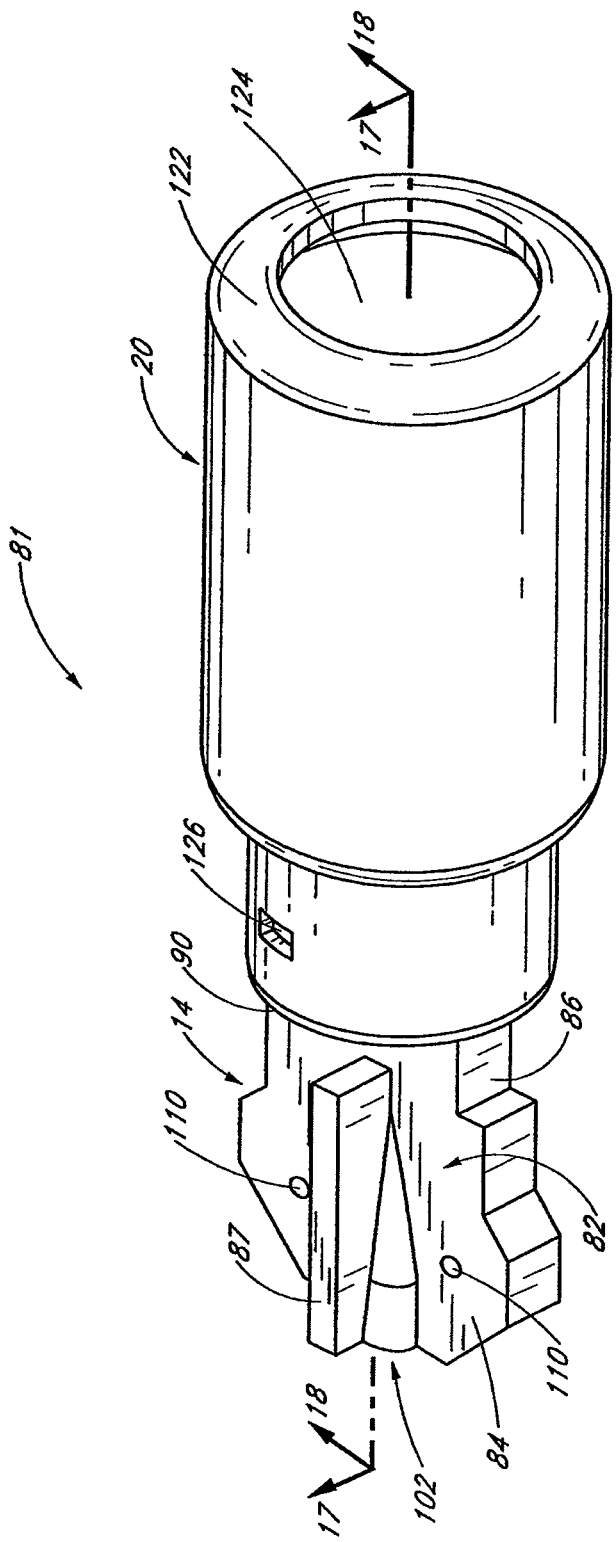
FIG. 16 is a perspective view of another embodiment of a flexible member including a valve member and a sleeve connected to the valve member.
Figure 18:
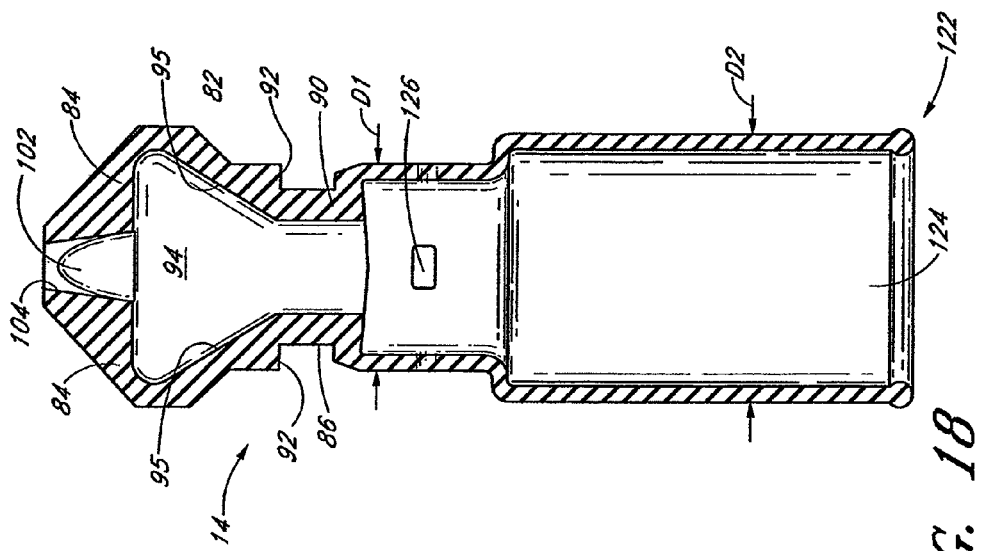
FIG. 18 is a cross-sectional view of the flexible member of FIG. 16, taken through line 18-18.
Figure 17:
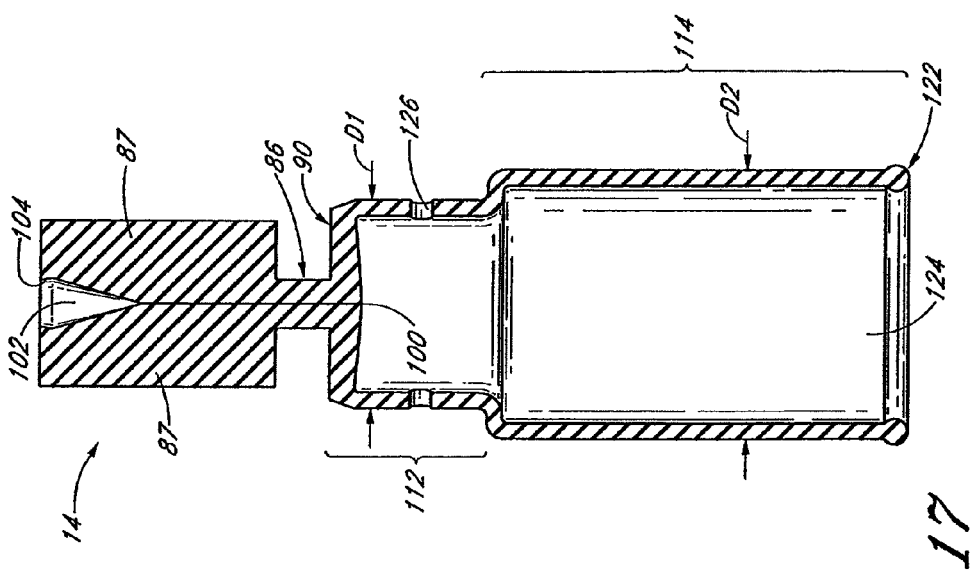
FIG. 17 is a cross-sectional view of the flexible member of FIG. 16, taken through line 17-17.

In the embodiments depicted in FIGS. 16-18, a flexible member 81 includes at least one stiffening rib 87 oriented substantially along a longitudinal axis of the valve member 14 and protruding transversely to the flat surfaces of the lateral extensions 84. FIG. 16 illustrates a perspective view of various embodiments of flexible member 81 including two stiffening ribs 87, and FIGS. 17 and 18 illustrate cut-away views of the flexible member 81 of FIG. 16. In the illustrated embodiments, the flexible member 81 is configured to be assembled with a housing lacking rings 60 as the flexible member 81 does not include any protrusions 120 (see FIGS. 12-14). In other embodiments, a flexible member can include both a stiffening rib 87 and protrusions 120 for application to a housing having rings 60 such as is illustrated in FIG. 2.

The stiffening ribs 87 can provide resiliency and durability to the valve member 14. In some embodiments, the ribs 87 can help the valve member 14 to resist crumpling in a substantially longitudinal direction upon insertion of a medical implement into the slit opening 100. Such crumpling could block or restrict fluid flow, prevent the connector from closing, or otherwise result in some degree of inconsistent performance. Since the crumpling tendency could be exacerbated by aging of a medical connector and repeated usage cycles, the stiffening ribs can greatly extend the lifespan of a valve member 14 in a medical connector. In some embodiments, additional structures and/or materials can be used in the medical connector 10, either in combination with or absent stiffening ribs 87, to resist crumpling of the valve member 14. For example, the valve member 14 may be constructed of a material selected to be flexible enough to permit insertion of a medical implement into the slit opening 100, but stiff enough to resist crumpling over repeated usage cycles. Likewise, a desired balance between flexibility and valve longevity and resistance to crumpling may be achieved by selecting a desired thickness of the valve member 14 (with relatively thicker material used in the valve member 14 increasing the valve longevity and crumple resistance at the expense of flexibility and ease of insertion of medical implements into the slit opening 100). For example, in some embodiments, the thickness of the wall of the valve member 14 across most, nearly all, or all of its outside surface area can be about as thick as the wall of the valve member 14 plus a stiffening rib 87. In some embodiments, the thickness of the wall of the valve member 14, in at least some regions, is at least as large as, or at least about 1½-2 times as large as, the diameter of the lead lumen 102.

Figure 19:
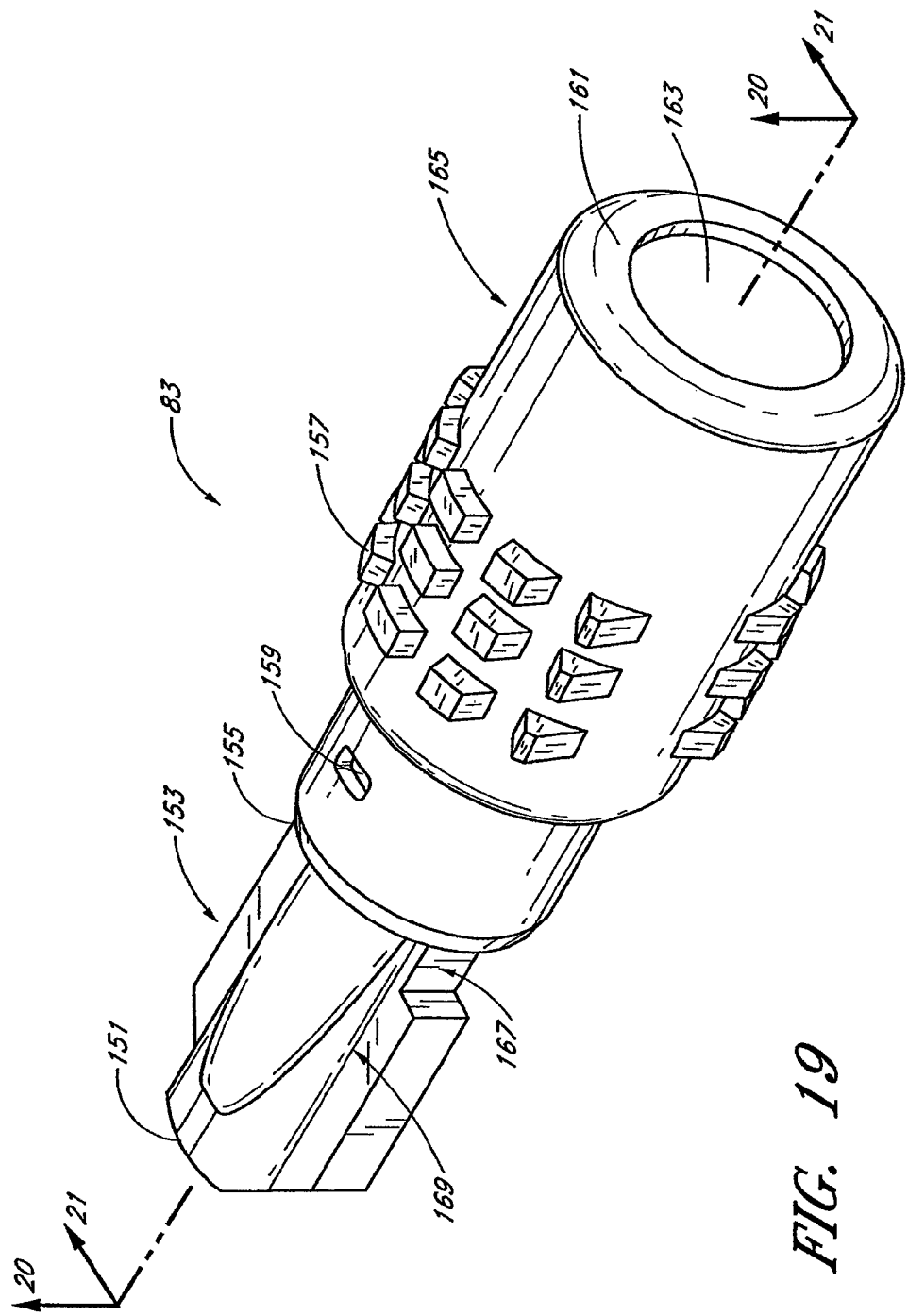
FIG. 19 is a perspective view of a third embodiment of a flexible member having a valve member and a sleeve connected to the valve member.
Figure 22:
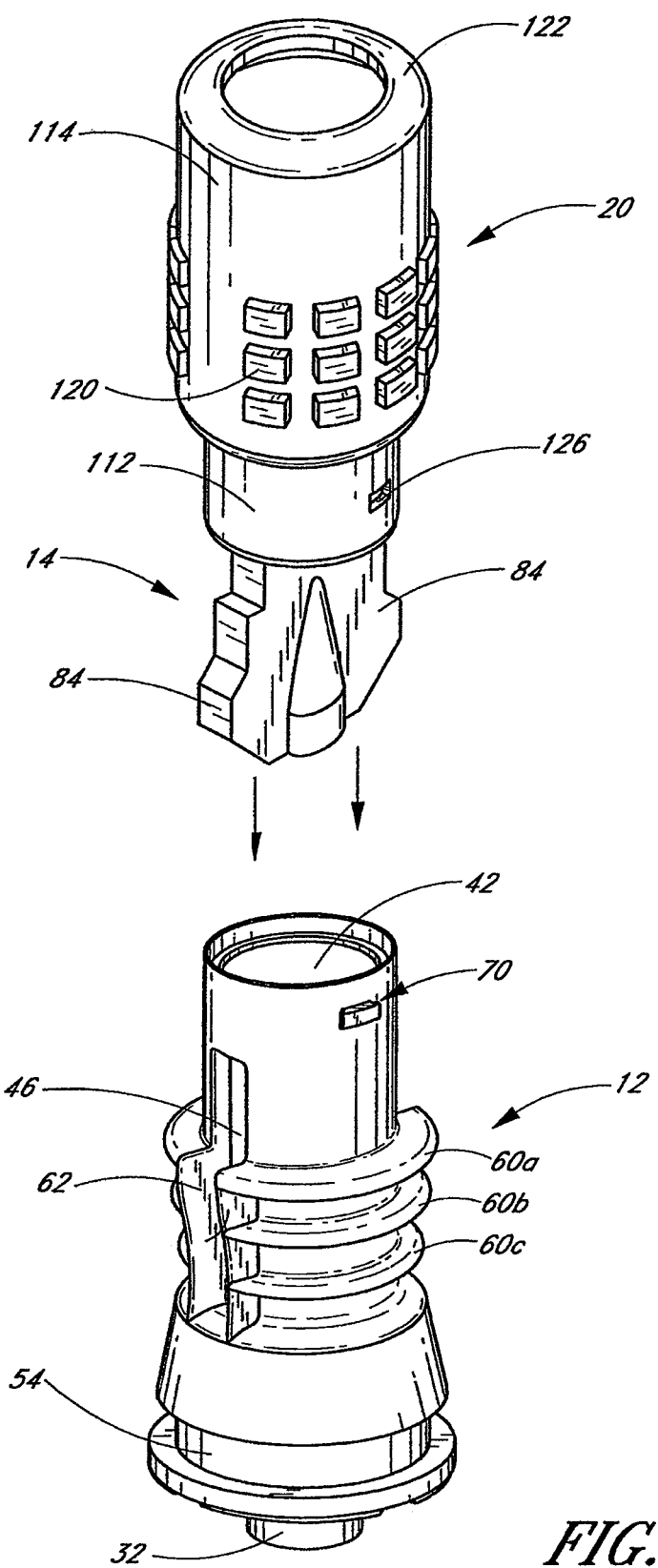
FIG. 22 is a perspective view illustrating an assembly of a flexible member with a housing member.

Another embodiment of flexible member 83 for use in a soft-grip medical connector that is configured to extend the usage lifespan of a valve member is illustrated in FIGS. 19-21. FIG. 19 illustrates a perspective view of the flexible member 83. As illustrated in FIG. 19, the flexible member 83 may share many external features with other embodiments of flexible member 80, 81 as previously discussed (including but not limited to those that are illustrated in FIGS. 19-21). For example, the flexible member 83 includes a valve member 153 and a sleeve 165. In certain embodiments, the sleeve 165 includes protrusions 157 for coupling with corresponding flanges on a housing. The sleeve 165 includes a constriction 161 surrounding an opening 163. The sleeve can include one or more windows 159 to accommodate and surround one or more protrusions 70 or other structures on the housing. The flexible member includes a transverse flange 155, a neck 167, and lateral extensions 169. As illustrated in FIGS. 20 and 21, the flexible member 83 includes a lead lumen 173 having a downstream opening 151.

As illustrated in FIGS. 20 and 21, which present cut-away views of the flexible member 83 of FIG. 19, the internal structure of the embodiments of flexible member 83 illustrated in FIGS. 19-21 can include features absent from other embodiments of flexible member 80, 81 illustrated herein. The valve member 153 of the flexible member comprises a pair of opposing sidewalls 177, 179 that intersect at an upstream end of the valve member 153 to form a slit 171 configured for insertion of a medical implement. In an undisturbed state, the slit 171 provides a sealed closure of the medical device to prevent the passage of fluid therethrough. In the downstream direction, the sidewalls 177, 179 diverge such that in an undisturbed state, a passage 175 defined by the valve member has a non-zero volume. Thus, unlike the previously-described flexible member 80, 81 embodiments, this flexible member 83 does not have a passage that is substantially planar in an undisturbed state.

In some embodiments, this non-zero volume of the passage 175 in an undisturbed state can prevent the illustrated embodiment of flexible member 83 from exhibiting positive flow characteristics when a medical implement inserted completely into the slit 171 is removed under certain circumstances. This passage 175 configuration has certain other advantages. As previously noted, the flexible member 83 resists crumpling. The divergence of the sidewalls 177, 179 enhances the durability of the valve member 153 as compared with planar sidewalls of other flexible member 80, 81 embodiments.

Additionally, the slit 171 of the flexible member 83 has a relatively small region of contact between the sidewalls 177, 179. The small region of contact results in a corresponding small resistance to flow in an undisturbed state. Thus, the flow through the valve member can be quickly initiated by inserting a medical implement only partially into the passage, or even merely positioning the medical implement adjacent to, but not within, the slit 171. Thus, either the tip of the implement or the pressure of the fluid flow breaks contact of the sidewalls 177, 179 at the slit 171 to open the valve. Advantageously, where partial insertion of, or merely adjacent contact with, a medical implement is performed, the valve member 153 may exhibit positive flow characteristics as the interior volume of the passage 175 in the undisturbed state is smaller than the interior volume of the passage 175 in the partially inserted state.

Furthermore, if, as in the illustrated flexible member 83, the passage 175 does not configured to provide positive flow characteristics on complete insertion of a medical implement, the passage 175 of the flexible member 83 need not include a region of relatively larger width. Thus, the passage 175 and the lateral extensions 169 of the flexible member 83 can be relatively narrow. Correspondingly, the housing can have a relatively smaller diameter as compared with a positive flow medical connector. Thus, a reduction in materials costs and connector weight could be achieved with a non-positive flow embodiment of flexible member 83.

Embodiments of methods for making the valve member 14 of the flexible connectors 80, 81 will now be discussed with reference to FIGS. 12-18. In general, a valve member 14 for use in the present system can be made according to any suitable process available to those of skill in this field. In some advantageous embodiments, the valve member 14 is built by molding first and second "pre-forms" 130 which are then placed face to face within a second mold. The pre-forms 130 are then over-molded in a separate molding process to form an integral flexible member 80 with valve member 14 and sleeve 20 portions such as those shown and described herein.

In one embodiment, a valve member 14 can be molded according to the general process described in U.S. Patent Application Publication No. 2004/0006330. A pair of preforms are molded between first and second mold pairs. After this initial molding step, the mold halves with the preforms still positioned therein, are pressed together with an overmold plate positioned between the mold halves. The overmold plate is generally configured to produce the final shape of the valve member 14. With the mold apparatus (including the preform mold halves and overmold plate) fully assembled, additional uncured material is then injected into the mold apparatus to fill the additional space in the mold cavity created by the overmold plate, thereby forming the remainder of the valve member 14. In some embodiments, the overmolding method described in the '330 publication can be adapted to form a valve member 14 with an integral sleeve as described herein. Alternatively, a valve member 14 can be molded according to the method of the '330 patent, and a sleeve 20 can be subsequently joined to the valve member 14 by any suitable process such as molding, welding, or adhesives.

Figure 15:
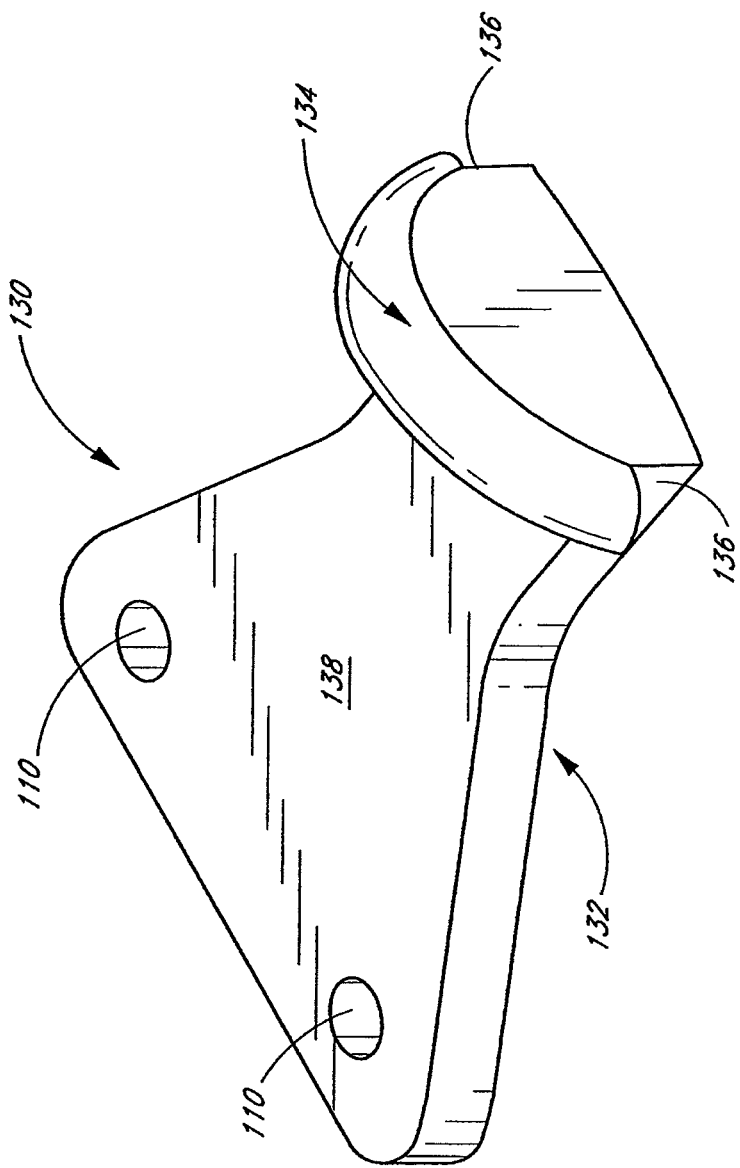
FIG. 15 is a perspective view of one embodiment of a preform for use in manufacturing some embodiments of a flexible member.

Another embodiment of an overmolding method is provided with reference to FIG. 15. According to this method, preforms 130 are molded and completely removed from their molds prior to performing an overmolding or joining step. FIG. 15 illustrates one embodiment of a preform 130 for use in forming a valve member 14. Each preform 130 has a generally planar face 132 that, in the completed valve member 14, forms a wall of the slit 94. A flange portion 134 is also integrally molded with each preform 132. The sides of the flange portion 134 can be set back from the face 132 of the planar portion in order to provide a space 136 for overmold material to flow between and connect the flange portions 134 of two preforms 130. The molding of the preforms 130 is typically accomplished by injecting a thermoset material into the cavity formed between the mold pairs and heating the molds and/or material to the set temperature of the specific material used. Pressure may be applied as needed to prevent material from leaking between the halves of the preform mold (not shown). In some embodiments, the preforms 130 can be provided with dimples 110 on a back side 138 opposite the face 132.

After each preform 130 is molded, it can be removed from the preform mold and placed into an over-mold. The overmold is generally configured to form a final desired valve member/sleeve structure 80. In some embodiments, an overmold comprises first and second halves. Each half can comprise pins configured to locate the preforms 130 in the overmold by aligning the pins with dimples 110 in the preforms 130.

Once the preforms are properly located in the overmold halves, the overmold halves can be brought together and an uncured overmolding material can be injected into the mold cavity. In some embodiments, the additional (overmolding) material is injected soon (i.e., a few seconds) after the preforms 130 are molded and while they are still somewhat hot from their initial molding. The additional material injected into the mold cavity bonds to the edges of the preforms 130 and forms the edges of the slit 94 in the completed valve member 14 and sleeve 20. In this way, the remainder of the valve member 14 and the sleeve 20 are overmolded and integrally formed with one another and with a pair of preforms during the over-molding step.

In some embodiments, the preforms 130 are pressed together with sufficient force during the overmolding process to prevent the overmolding material from migrating between the contacting surfaces of the preforms 130. This preserves the patency of the slit 94 by preventing the contacting faces of the preforms 130 from bonding to each other during the overmold step.

In other embodiments of this method, additional material is allowed to flow between and bond the contacting faces of the preforms to one another. Subsequently, the valve member 14 can be re-opened by inserting a blade between the preforms, thereby cutting open the slit 94. In still another embodiment, the entire valve member/sleeve structure can be molded in a single process (i.e. without a pre-formed slit), and a slit 94 can be subsequently formed by inserting a blade into a solid valve member section. In another alternative embodiment, a sleeve 20 and valve member 14 can be individually pre-formed and subsequently attached to one another, such as by overmolding, welding or with adhesives.

In some embodiments, the material added in the overmold step is similar to that utilized in molding the preforms 130. However, in other embodiments the preform material and the overmold material may comprise different but nonetheless suitable materials for manufacturing the valve member 14 and sleeve 20.

In general, the sleeve 20 is typically made of a material with sufficient flexibility to allow the sleeve 20 to be inverted and stretched around the housing 12, and sufficient resilience to tightly grip the housing 12 in the inverted orientation. Similarly, the valve member 14 is typically made of a material that is sufficiently flexible to allow a cannula to be inserted therein to open the slit, and also has sufficient resilience to re-close the valve member 14 once the cannula is withdrawn. In some embodiments, the valve member 14 and the sleeve 20 are unitarily formed of an elastomeric material such as silicone rubber. In one preferred embodiment, the valve member 14 and sleeve 20 are integrally molded from 50 durometer silicone rubber. Alternatively, the valve member 14 and sleeve 20 can be made of synthetic polyisoprene, other silicone rubber and/or urethane formulations, or other materials acceptable for medical use. In some embodiments, the sleeve 20 can be molded from a first material, and the valve member 14 can be molded from a second, different material.

Some embodiments of a flexible member 83 (FIGS. 19-21) not including positive flow characteristics can be more efficiently manufactured. The manufacture of a flexible member 83 as illustrated in FIGS. 19-21 can be accomplished with fewer steps and, accordingly, lower costs than other embodiments featuring positive flow functionality. The relatively small region of contact between the sidewalls 177, 179 facilitates manufacture of the flexible member 83 embodiments illustrated in FIGS. 19-21.

With reference now to FIGS. 22-25, embodiments of a method of assembling a soft grip medical connector 10 will be described. The valve member 14 can be inserted into the upper housing cavity 42 portion of the housing 12 by partially folding or compressing the lateral extensions 84 inwards and pushing the valve member 14 into the upper housing cavity 42 until the compressed or folded lateral extensions 84 reach the slots 46 and are permitted to uncompress or unfold and extend through the slots 46 to the outside of the housing 12. In some embodiments, tooling can be employed to grasp the lateral extensions 84 and pull the valve member 14 into the upper housing cavity 42. In some of these embodiments, the tool can be configured to engage the dimples 110 in the lateral extensions 84 to grasp and pull the valve member 14. As the lateral extensions 84 are aligned and pulled or pushed through the slots 46, an additional downward force can be applied to slightly stretch the valve member 14 and allow the shoulders 92 to engage the top edges 140 of the slots 46. In this way, a preload (discussed in further detail below) can be applied to the valve member 14. This downward force also allows the lead lumen to more securely engage the interior cannula 50 within the housing 12.

Once the valve member 14 is fully inserted into the upper housing 40 (e.g. as shown in FIG. 25), the sleeve portion 20 can be inverted and stretched over the housing 12. This can be accomplished using any suitable tooling. The sleeve 20 can also be grasped by a person's fingers and pulled outwards and downwards in the direction of the arrows 146 in FIG. 23. As the sleeve 20 is inverted, the protrusions 120 will generally align with the spaces between the rings 60 of the housing 12. If provided, the windows 126 will also be aligned with the protrusions 70 so that the protrusions 70 pass through and extend beyond the flexible member 80.

When a cleaning solution or other liquid is applied to the medical connector 10, the liquid may seep around the protrusions 70 between the sleeve 20 and the housing 12, thus causing the sleeve to slip relative to the housing 12 and making it more difficult for a health care professional to grip the outside surface of the medical connector 10. To reduce the risk that the sleeve 20 will slide or separate from the housing 12, the sleeve 20 can be adhered to the housing 12. Additionally, in various embodiments, the sleeve 20 may be stretched over an annular groove 54 (FIG. 24) or sandwiched in a space 61 between housing portions 41, 51 (FIGS. 10, 11) to reduce the risk of slippage. Before the sleeve 20 is inverted and stretched over the housing 12, an adhesive can be applied to the housing 12 or the sleeve 20 in a location of contact between the sleeve 20 and the housing 12 of an assembled connector 10. For example, in certain embodiments, the housing may include a recess 73 (FIG. 11) adjacent the Luer lugs 71 to which adhesive may be applied. Alternatively, adhesive may be spread over an outer surface of the housing 12.

Preferably, the housing 12, sleeve 20, and adhesive are chosen of compatible materials to reduce the risk of material degradation due to the application of adhesive. For example, the sleeve 20 can be constructed of a silicone rubber, to be bonded with the housing 12 with a silicone-based adhesive such as an adhesive comprising dimethylpolysiloxane. In certain embodiments, the adhesive may require the mixture of two components, at least one of which includes a catalyst such as a platinum-based catalyst. In certain embodiments, the adhesive may require curing such as, for example, by heating the adhesive to a predetermined temperature for a predetermined time. For material compatibility with a silicone-based adhesive, the housing 12 can be constructed of a glass-reinforced thermoplastic polyester resin, such as, for example, glass-filled Valox® including approximately 30% glass fill, produced by General Electric Company. In some embodiments, the housing 12 can be constructed of a polycarbonate material, although in some situations the polycarbonate may not be compatible with a silicone-based adhesive.

FIGS. 24 and 25 illustrate cross-sectional views of embodiments of a fully assembled soft grip medical connector 10. In the illustrated embodiment, the sleeve 20 fully surrounds the housing 12 including the upper housing 40, the rings 60, and a substantial portion of the Luer skirt 52. But, it is contemplated that in other embodiments, the sleeve 20 may extend over a portion of the housing 12. For example, in certain embodiments, the sleeve may extend from the upstream end 16 of the housing 12 downward over between approximately one-half a height of the upper housing 40 and the entire upper housing 40. In other embodiments, the sleeve 20 may extend from the upstream end 16 of the housing 12 downward over between approximately one-fourth the height of the upper housing 40 to one-half the height of the upper housing 40.

Likewise, in embodiments of medical connector 10 including a two-piece housing, as illustrated in FIGS. 7-11, in various embodiments, the sleeve 20 can surround a portion of the first housing portion 41, substantially all of the first housing portion 41, all of the first housing portion and a portion of the second housing portion 51, or all of the first housing portion and substantially all of the second housing portion 51. The sleeve 20 can also surround the lateral extensions 84 extending through the slots 46 of the housing 12.

FIGS. 24 and 25 illustrate an example of an assembled connector in a sealed state (i.e., in which fluid flow through the connector is impeded). The valve member 14 is positioned within the upper housing cavity 42 of the housing 12, with the first and second lateral extensions 84 of the valve member 14 protruding from the first and second slots 46 in the housing 12. The lead lumen 102 of the valve member 14 is positioned so that the interior cannula 50 extends at least partway into the lead lumen 102 of the valve member 14, facilitating fluid communication between the valve member 14 and the Luer cannula 32 when the connector is in the open state (as illustrated in FIGS. 15 and 16). The flange 90 covers the axial opening at the upstream end 16 of the housing 12.

The sleeve 20 on the outside surface of the housing 12 allows health care providers to more comfortably and effectively grasp the connector 10. The flexible material of the sleeve 20 provides a softer surface for the fingers. There is preferably a high-friction interface between the flexible material of the sleeve 20 and the rubber gloves typically worn by health care providers, requiring less finger-pinching effort to screw the connector 10 onto a catheter or other medical implement and to maintain the connector 10 in a desired position and orientation during the connection and fluid-administration processes.

In addition to providing a soft, easily grippable outer surface, the sleeve 20 surrounding the exterior of the housing 12 protects the lateral extensions from being pinched or otherwise undesirably manipulated during handling and use of the connector. In one embodiment, the valve member 14 and housing 12 are constructed such that the distance between the upstream end 16 and the top edges 140 of the slots 46 of the housing 12 is slightly larger than the distance between the flange 90 and the shoulders 92 of the lateral extensions 84 of the valve member 14. This arrangement results in the application of a tensile force or preload to the valve member 14 between the flange 90 and the lateral extensions 84.

The preload arises as the shoulders 92 bear against the top edges 140 of the housing and the seal flange 90 bears against the upstream end 16 and/or the shoulder 142 of the axial opening at the upstream end of the housing. In some embodiments, the preload causes the flange 90 to assume a slightly bowl-shaped or concave configuration as the edges of the upstream housing end 16 bear against the underside of the flange 90. The bowl-shaped flange 90 tends to more tightly pinch closed the slit opening 100 and thus enhances the ability of the valve member 14 to prevent fluid flow. The preload also prevents buckling of the valve member 14 along its longitudinal axis and maintains the sides of the slit 94 in close proximity to each other along their entire length. The preload thus promotes a relatively thin slit 94 below the flange 90, which enhances the sealing performance of the slit 94. In some embodiments, a distance between the shoulders 92 and the opening 148 of the interior cannula 50 is sized such that the lead lumen 102 of the valve member 14 will be engaged with and sealed to the interior cannula 50 of the housing 12.

Figure 27:
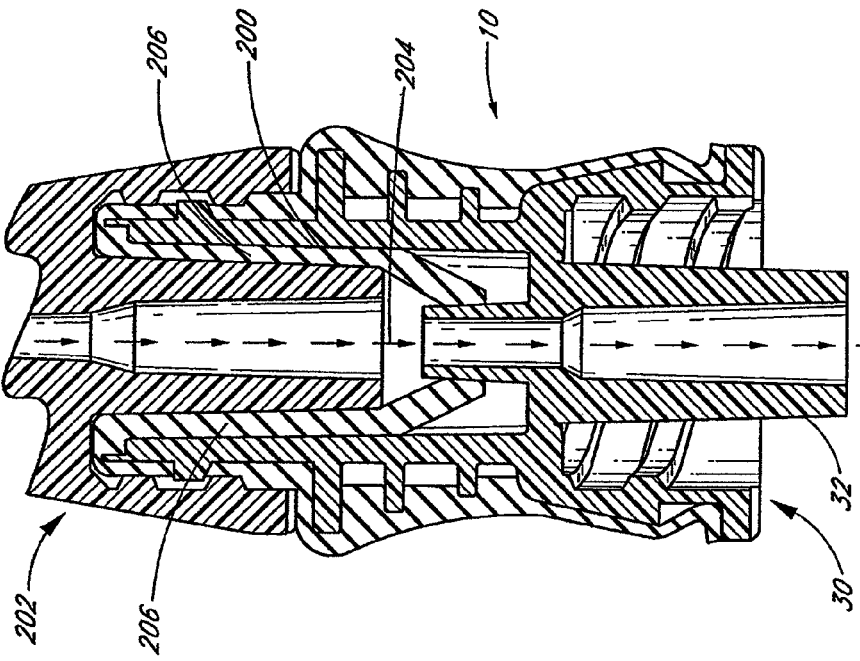
FIG. 27 is a cross-sectional view of the connector of FIG. 24 taken at about 90° relative to the cross-section of FIG. 26.
Figure 26:
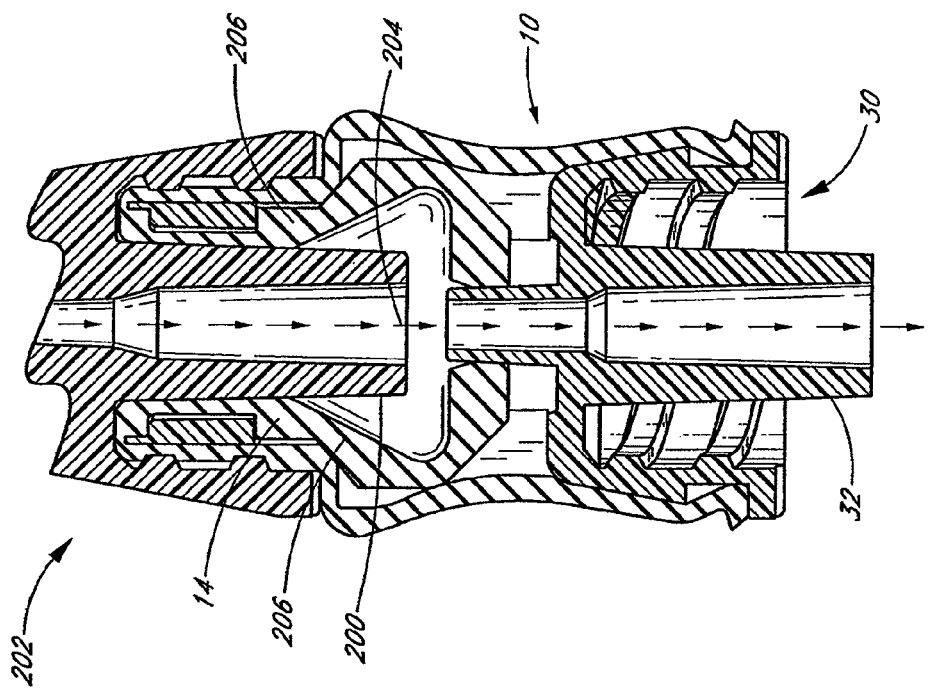
FIG. 26 is a cross-sectional view of the connector of FIG. 24 with a syringe connected thereto.

Referring now to FIGS. 26 and 27, during use of the connector 10, a cannula 200 of a medical device 202, such a syringe, can be inserted into the valve member 14 of the connector 10, thereby opening the valve member 14 to fluid flow 204 between the medical device 202 and the Luer cannula 32 of the connector 10.

Before the cannula 200 is inserted, the connector 10 is in a sealed state (see, e.g., FIGS. 24 and 25). In this state, the slit 94 defines a substantially closed or highly restricted flow path through the valve member 14. As illustrated in FIG. 16, when the cannula 200 is inserted through the slit 94, the valve member 14 opens a fluid flow path within the connector 10 while exerting an inwardly directed force against the cannula 200 of the medical device 202, preferably forming a tight seal around the circumference of the cannula 200 to prevent leakage of fluid through the upstream end of the connector 10. The insertion of the cannula 200 into the valve member 14 also causes the valve member 14 to stretch in the downstream direction over the interior cannula 50.

As fluid is injected from the medical device 202, through the cannula 200, and into the interior space within the valve member 14, the space between the slits walls 206 increases further and the slit walls 206 expand further and lengthen further in the downstream direction. The valve member 14 thus selectively permits fluid 204 to flow between a medical device 202 on the upstream end of the connector 10 and a medical implement (not shown) to which the lower Luer connector 30 is attached.

As shown in FIGS. 26 and 27, when in an open state, the connector 10 permits fluid flow 204 that is preferably substantially unobstructed and linear. This generally allows the connector to achieve higher flow rates. In some embodiments, the fluid flow rates through the connector 10 can exceed 600 cubic centimeters per minute. In addition, the unobstructed and linear fluid flow 204 interferes less with the inherent qualities of the flowing fluid 204. For example, if the fluid flow 204 is blood, the various blood cells and other constituents are less likely to break down within the illustrated connector 10 as compared to a connector in which there is a circuitous fluid flow path with fluid turbulently strikes against hard and/or angular internal surfaces.

As the fluid flow 204 diminishes and/or the cannula 200 of the medical device 202 is withdrawn from the valve member 14, the slit walls 206 retract and return to their original configuration to once again define a narrow, restrictive path width between them (as illustrated, for example, in FIGS. 24 and 25). This retraction of the slit walls 206 causes the volume within the slit 94 to decrease to a certain minimum. The retracting action of the slit walls 206 also forces out the remaining fluid in the area between the walls 206. As the syringe cannula 200 is being withdrawn, the displaced fluid cannot flow out of the slit 94 through the upstream end of the valve member 14 because this space is occupied by the syringe cannula 200. The resilient narrow neck 97 of the slit 94 preferably blocks any significant flow of fluid between the outer surface of the cannula 200 and the inner surface of the flexible member 80 by forming a tight seal around the circumference of the cannula 200. Thus, the displaced fluid is instead forced downwardly from the slit 94, through the interior cannula 50 and downwardly directed cannula 32, and ultimately out of the housing 12. This advantageously results in automatic positive flow from the connector 10 toward the patient upon withdrawal of the medical device 202 from the upstream end of the connector 10, and avoids or minimizes retrograde fluid flow toward the connector 10 and away from the patient.

Although the foregoing description refers to a syringe, it is contemplated that any type of suitable medical devices may be joined to either end of the connector 10, such as IV bags, other connectors, and tubing, for the purposes of fluid transfer or for any other desired purpose. An auxiliary connector also may be connected to the soft grip connector, and both connectors can be placed in fluid communication with a catheter with an end positioned within a patient. This arrangement can provide several advantages in situations which call for the use of a unique auxiliary connector. For example, when it is necessary to replace or reconfigure fluid lines connected to auxiliary connectors, such lines may be removed from fluid communication with the catheter without creating a backflow in the catheter, and replaced with a similar connector or any other medical implement. In some embodiments, one such auxiliary connector may be the CLAVE® connector sold by ICU Medical, Inc. However, any connector or other medical implement or device may be placed in fluid communication with the soft grip connector 10 to introduce fluid to the patient or to withdraw blood from the patient including, but not limited to, pierceable connectors, needle-less connectors, medical tubing, syringes or any other medical implement or device.

Although certain embodiments and examples have been described herein, it will be understood by those skilled in the art that many aspects of the methods and devices shown and described in the present disclosure may be differently combined and/or modified to form still further embodiments. For example, the various embodiments of housing may be interchangeable applied to the various embodiments of flexible member to achieve multiple embodiments of soft-grip medical connector. Additionally, it will be recognized that the methods described herein may be practiced using any device suitable for performing the recited steps. Such alternative embodiments and/or uses of the methods and devices described above and obvious modifications and equivalents thereof are intended to be within the scope of the present disclosure. Thus, it is intended that the scope of the present invention should not be limited by the particular embodiments described above, but should be determined only by a fair reading of the claims that follow.

What is claimed is:

1. A medical connector for selectively permitting fluid to flow between a first medical device and a second medical device, the medical connector comprising:
    a housing comprising an upstream end adapted to receive the second medical device, a downstream end with an interface configured to receive the first medical device, an outer surface, a base member with an annular surface, an upper housing cavity extending from the upstream end of the housing to the annular surface of the base member, and an interior cannula extending from the annular surface toward the upstream end of the housing; and
    a valve member at least partially positioned within the housing, the valve member configured to control a flow of fluid through the housing, the valve member comprising a seal body made of a flexible material, the seal body having a downstream end, an upstream end configured to receive at least a portion of the second medical device, and a normally closed passage in fluid communication with the downstream end of the seal body and the upstream end of the seal body, the seal body comprising a first sidewall and a second sidewall, the second sidewall opposing the first sidewall, the first and second sidewalls diverging in a downstream direction such that the passage has a non-zero volume when in an undisturbed state in which a first end of the second medical device is not in contact with the upstream end of the seal body;
    wherein the valve member comprises a lead lumen at the downstream end of the seal body configured to fit over an outside surface of the interior cannula such that the downstream end of the seal body is separated from the annular surface of the base member by a first distance when the valve member is in a closed state, and wherein, upon insertion of the portion of the second medical device into the passage, the downstream end of the seal body slides in the downstream direction along the outer surface of the interior cannula such that the downstream end of the seal body is separated from the annular surface of the base member by a second distance, the first distance being greater than the second distance;
    wherein the valve member comprises a transverse flange having a slit opening therethrough in fluid communication with the passage; and
    wherein the valve member comprises shoulders configured to engage corresponding edges of the housing, wherein the distance between the upstream end of the housing and the edges is greater than the distance between the transverse flange and the shoulders, such that the valve member is under a preload when the shoulders engage the edges causing the transverse flange to bear on the upstream end of the housing.

2. The connector of claim 1, wherein the housing comprises an upstream housing portion containing the valve member and a downstream housing portion configured to be mateably coupled to the upstream housing portion.

3. The connector of claim 2, wherein the upstream housing portion comprises one or more alignment features, and wherein the downstream housing portion comprises one or more alignment features configured to engage the one or more alignment features of the upstream housing portion to align the upstream housing portion with the downstream housing portion.

4. The connector of claim 1, wherein the housing comprises protrusions on an upper portion thereof, the protrusions configured to engage internal threads of a Luer connector for securing the second medical device to an upstream end of the connector.

5. The connector of claim 1, wherein the housing is constructed of a polycarbonate material.

6. The connector of claim 1, wherein the housing is constructed of a glass-reinforced thermoplastic polyester resin.

7. The connector of claim 1, wherein the seal body is made of silicone rubber.

8. The connector of claim 1, wherein the valve member is constructed of silicone rubber.

9. The connector of claim 1, wherein the housing comprises an hourglass-shaped profile.

10. The connector of claim 1, wherein the connector comprises an hourglass-shaped profile.

11. The connector of claim 1, wherein the valve member comprises features arranged to interact with features of the housing in order to limit movement of the valve member relative to the housing.

12. The connector of claim 1, wherein the housing further comprises at least one vent configured to ventilate the upper housing cavity.

13. The connector of claim 1, wherein a lower surface of the housing comprises at least one vent configured to allow air flow into and out of a Luer lock cavity within the housing when a lower portion of the connector is joined to the first medical device.

14. The connector of claim 1, wherein the valve member is configured to force a volume of fluid downwards through the interior cannula upon removal of the second medical device from the upstream end of the housing.

15. The connector of claim 14, wherein the passage is adapted to have a relatively small interior volume when in an undisturbed state and a larger interior volume upon the introduction of the portion of the second medical device into the passage, the passage adapted to retract to define a restricted flow path and a relatively small interior volume upon the withdrawal of the portion of the second medical device from the passage, at least a portion of the upstream end of the seal body adapted to initially press against the inserted portion of the second medical device as the second medical device is withdrawn, so that a fluid occupying the interior volume is forced toward the downstream end of the seal body as the passage retracts.

16. The connector of claim 15, wherein the seal body further comprises at least one rib on an outer surface of the seal body, the rib extending transversely relative to the passage and spanning longitudinally from the region near the upstream end of the seal body to the region near the downstream end of the seal body.

17. The connector of claim 1, wherein the valve member is adhered to the housing in order to limit movement of the valve member relative to the housing.

18. The connector of claim 1, wherein the valve member further defines an unobstructed linear flow path when the second medical device is inserted into the medical connector.

19. The connector of claim 1, wherein the medical connector is configured to selectively permit an unobstructed linear flow of fluid therethrough.

20. The connector of claim 1, wherein the passage is configured to selectively permit an unobstructed flow of fluid therethrough at a flow rate of at least approximately 600 cubic centimeters per minute.

21. The connector of claim 1, wherein the first and second sidewalls are configured to separate to expand the passage when a fluid is flowing through the valve member.

22. The connector of claim 1, wherein the seal body comprises a neck portion positioned in a region near the upstream end of the seal body, the passage being relatively narrow in the region of the upstream end of the seal body.

23. The connector of claim 22, wherein the transverse flange extends from the neck portion towards the housing.

24. The connector of claim 1, wherein the upstream end and the downstream end of the housing are disposed on the same axis to assist in providing a straight fluid-flow path through the medical connector.

25. The connector of claim 1, wherein the first sidewall and the second sidewall define a region of contact at an upstream end of the valve member at least when the valve member is in a closed state.

26. The connector of claim 25, wherein the region of contact between the first sidewall and the second sidewall is relatively small to facilitate opening of the medical connector.

27. The connector of claim 1, wherein the upstream end of the housing and the downstream end of the housing are disposed on the same axis to assist in providing a straight fluid flow path through the medical connector, wherein the first sidewall and the second sidewall define a region of contact at the upstream end of the seal body at least when the valve member is in a closed state, the region of contact between the first sidewall and the second sidewall being relatively small to facilitate opening of the medical connector, and wherein the passage is configured to selectively permit an unobstructed flow of fluid therethrough at a flow rate of at least approximately 600 cubic centimeters per minute.

28. The connector of claim 1, wherein at least one of the first sidewall and the second sidewall has a lateral thickness that increases in the downstream direction along the length of the seal body.

29. The connector of claim 1, wherein the transverse flange bears on the upstream end of the housing such that the valve member is preloaded towards a closed position.

30. The connector of claim 1, wherein the transverse flange has a concave configuration to bias the slit opening towards a closed position when in a closed state.

\* \* \* \* \*